(12) United States Patent
Naito

(10) Patent No.: US 10,303,826 B2
(45) Date of Patent: May 28, 2019

(54) METHOD FOR CREATING FINITE ELEMENT MODEL FOR FILLER-CONTAINING RUBBER

(71) Applicant: SUMITOMO RUBBER INDUSTRIES, LTD., Kobe-shi, Hyogo (JP)

(72) Inventor: Masato Naito, Kobe (JP)

(73) Assignee: SUMITOMO RUBBER INDUSTRIES, LTD., Kobe-shi, Hyogo (JP)

(*) Notice: Subject to any disclaimer, the term of this patent is extended or adjusted under 35 U.S.C. 154(b) by 514 days.

(21) Appl. No.: 15/022,518

(22) PCT Filed: Aug. 21, 2014

(86) PCT No.: PCT/JP2014/071840
§ 371 (c)(1),
(2) Date: Mar. 16, 2016

(87) PCT Pub. No.: WO2015/052996
PCT Pub. Date: Apr. 16, 2015

(65) Prior Publication Data
US 2016/0232263 A1    Aug. 11, 2016

(30) Foreign Application Priority Data

Oct. 7, 2013  (JP) .................................. 2013-210412
Feb. 28, 2014 (JP) .................................. 2014-039102

(51) Int. Cl.
*G06F 17/50* (2006.01)
*C08K 3/013* (2018.01)
*G06F 19/00* (2018.01)

(52) U.S. Cl.
CPC .......... *G06F 17/5018* (2013.01); *C08K 3/013* (2018.01); *G06F 19/70* (2013.01); *G06F 2217/44* (2013.01)

(58) Field of Classification Search
CPC .. G06F 17/5018; G06F 19/70; G06F 2217/44; C08K 3/013
See application file for complete search history.

(56) References Cited

U.S. PATENT DOCUMENTS 7,292,966 B2 * 11/2007 Naito .................. G06F 17/5018
                                                            703/6
7,415,398 B2 *  8/2008 Naito .................. G06F 17/5018
                                                            703/1
(Continued)

FOREIGN PATENT DOCUMENTS

EP       2 498 192 A2    9/2012
JP     2005-121535 A     5/2005
(Continued)

OTHER PUBLICATIONS

Möller, C. & Sundlo, O. "Method for merging scales in Finite element analyses" Masters Thesis Chalmers U. (2017) (Year: 2017).*
(Continued)

*Primary Examiner* — Jay Hann
(74) *Attorney, Agent, or Firm* — Birch, Stewart, Kolasch & Birch, LLP

(57) ABSTRACT

A method for creating a finite element model of a filler compounded rubber including a filler dispersed in a matrix rubber, including a first step of defining a filler model in which the filler is discretized using a finite number of elements, a second step of defining a matrix rubber model independently of the filler model, the matrix rubber model being created by discretizing a space in which at least the matrix rubber occupies using a finite number of elements, and a model-embedded step of embedding the filler-model (Continued)

in the matrix rubber model. The model-embedded step includes overlapping the filler-model with the matrix rubber model without considering sharing of the respective nodes of the filler model and the matrix rubber model, and defining a filler compounded rubber model by providing a constraint condition to at least a boundary between the filler and matrix rubber models.

20 Claims, 31 Drawing Sheets

(56) References Cited

U.S. PATENT DOCUMENTS

| | | | |
|---|---|---|---|
| 8,380,776 B2* | 2/2013 | Suzuki | G06F 17/5018 703/5 |
| 9,002,687 B2* | 4/2015 | Hamatani | G06F 17/5018 703/1 |
| 2005/0086034 A1 | 4/2005 | Naito et al. | |
| 2009/0228254 A1 | 9/2009 | Seto et al. | |
| 2012/0232848 A1 | 9/2012 | Naito | |
| 2012/0239351 A1 | 9/2012 | Naito | |
| 2013/0085727 A1 | 4/2013 | Wu | |
| 2014/0257783 A1 | 9/2014 | Naito | |

FOREIGN PATENT DOCUMENTS

| | | |
|---|---|---|
| JP | 2009-193339 A | 8/2009 |
| JP | 2012-185733 A | 9/2012 |
| JP | 2012-198654 A | 10/2012 |
| JP | 2012-221472 A | 11/2012 |
| JP | 2013-89124 A | 11/2012 |

OTHER PUBLICATIONS

Extended European Search Report, dated May 18, 2017, for European Application No. 14852347.5.

Gurrum et al., "Inclusion Interaction and Effective Material Properties in a Particle-filled Composite Material System," J Mater Sci, vol. 46, No. 1, 2011 (Published Online Aug. 27, 2010), pp. 101-107, XP-19869166A.

Krebs et al., "Method to Connect Nonconforming Mesh in 3-D With the Overlapping Method," IEEE Transactions on Magnetics, vol. 45, No. 3, Mar. 2009 (Mar. 1, 2009), pp. 1420-1423, XP-11252393A.

Krebs et al., "Overlapping Finite Elements Used to Connect Non-Conforming Meshes in 3-D With a Vector Potential Formulation," IEEE Transactions on Magnetics, vol. 47, No. 5, May 2011 (May 1, 2011), pp. 1218-1221, XP-11354243A.

* cited by examiner

FIG.5
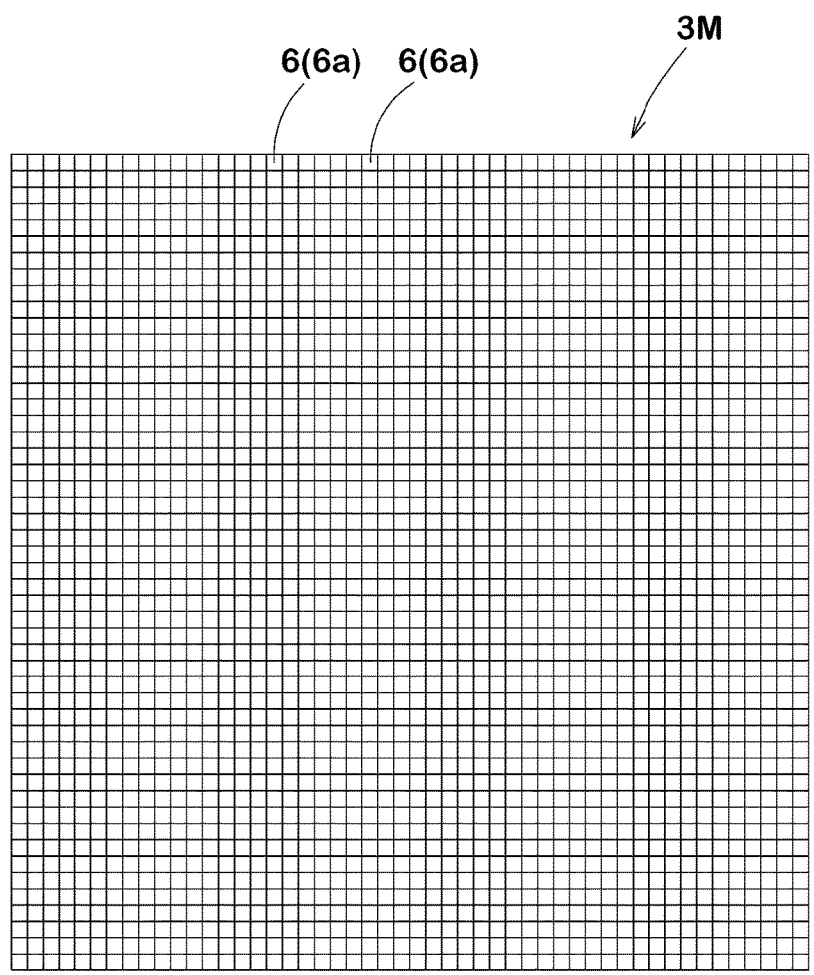
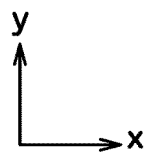

METHOD FOR CREATING FINITE ELEMENT MODEL FOR FILLER-CONTAINING RUBBER

TECHNICAL FIELD

The present invention relates to a method for creating a finite element model of a filler compounded rubber that can save the time and effort for creating thereof.

BACKGROUND ART

In recent years, various computer simulations using a finite element method have been conducted. In these simulations, a finite element model is created by discretizing an object to be analyzed using a finite number of elements that can be handled by a computer. The finite element model is inputted a characteristic representing the stiffness and viscosity thereof. In the computer simulation using the finite element method, displacement of each node is calculated based on the predetermined deformation condition or the like.

In recent years, a computer simulation using the finite element method is used in not only a mechanical structure but also in a development of a rubber material. For example, in order to streamline the development of a filler for reinforcing rubber, the following Patent Documents 1 and 2 have proposed a method for creating a finite element model of a filler compounded rubber including the filler dispersed in the matrix rubber with a computer.

In Patent Document 1 and Patent Document 2, the respective portions occupied by the matrix rubber and the filler, for example, are identified based on a microscopic cross-section photograph of the filler compounded rubber. The respective portions, for example, are modeled into a matrix rubber model and a filler model using two-dimensional elements such as a triangle or quadrilateral.

Patent document 1: Japanese Unexamined Patent Application Publication No. 2012-185733
Patent document 2: Japanese Unexamined Patent Application Publication No. 2012-198654

SUMMARY OF INVENTION

Technical Problem

When the filler profile is complicated, in order to model accurately it, it is necessary to discretize the filler using a small sized element. Meanwhile, in order to reduce the computational cost, it is desirable to reduce the number of elements by discretizing the matrix rubber using a large sized element. Unfortunately, in the above conventional method, the nodes of each element were shared at a boundary between the matrix rubber model and the filler model. Therefore, there was a problem where the resolution of one of the models is restricted by the resolution of the other model.

For example, in order to increase the calculation accuracy, when the matrix rubber model is discretized to fit the resolution of the filler, the computational cost tends to increase. On the other hand, in order to reduce the computational cost, when the filler model is discretized to fit the resolution of the matrix rubber model, the calculation accuracy tends to decrease.

The present invention has been made in view of circumstances described above, and has a main object to provide a method for creating a finite element model of a filler compounded rubber that may prevent an increase in the computational cost.

Solution to Problem

The present invention provides a method for creating a finite element model of a filler compounded rubber comprising a filler dispersed in a matrix rubber using a computer, the method comprising a first step of defining a filler model in which the filler is discretized using a finite number of elements, a second step of defining a matrix rubber model independently of the filler model, the matrix rubber model being created by discretizing a space in which at least the matrix rubber occupies using a finite number of elements, and a model-embedded step of embedding the filler-model in the matrix rubber model. The model-embedded step comprises a step of overlapping the filler-model with the matrix rubber model without considering sharing of the respective nodes of the filler model and the matrix rubber model, and a step of defining a filler compounded rubber model by providing a constraint condition to at least a boundary between the filler model and the matrix rubber model.

In the method for creating a finite element model of a filler compounded rubber according to the invention, preferably, the matrix rubber model is obtained by discretizing a space that comprises a first space in which the matrix rubber occupies and a second space in which the filler occupies, and the model-embedded step comprises the step of defining the constraint condition between the filler model and the matrix rubber model to the second space.

In the method for creating a finite element model of a filler compounded rubber according to the invention, preferably, the filler comprises an aggregate of a plurality of primary particles, and the first step comprises a step of defining a plurality of primary particle models each obtained by discretizing each primary particle of the filler using a finite number of elements independently of the matrix rubber model and a step of overlapping the primary particle models one another partially without considering sharing of the respective nodes of the primary particle models.

In the method for creating a finite element model of a filler compounded rubber according to the invention, preferably, the filler compounded rubber model comprises a three-dimensional model, the matrix rubber model is obtained by discretizing the space using a three-dimensional element, and each primary particle model is obtained by discretizing only an outer surface of each primary particle using a two-dimensional element.

In the method for creating a finite element model of a filler compounded rubber according to the invention, preferably, the filler compounded rubber model comprises a three-dimensional model, and the matrix rubber model and the primary particle models are obtained by discretizing using the elements of three-dimensional.

In the method for creating a finite element model of a filler compounded rubber according to the invention, preferably, the elements of the matrix rubber model have different size to the elements of the primary particle models.

In the method for creating a finite element model of a filler compounded rubber according to the invention, preferably, the method further comprises a third step of defining an interface layer model obtained by modeling at least one interface layer surrounding the filler independently of the filler model and the matrix rubber model, the third step comprises a step of discretizing the interface layer using a finite number of elements, and the model-embedded step comprises the step of overlapping the interface layer model with the matrix rubber model without considering sharing of the respective nodes of the inter face layer model and the matrix rubber model.

In the method for creating a finite element model of a filler compounded rubber according to the invention, preferably, the model-embedded step comprises the step of defining a constraint condition to at least a boundary between the interface layer model and the matrix rubber model.

In the method for creating a finite element model of a filler compounded rubber according to the invention, preferably, the interface layer model is obtained by discretizing the interface layer using the elements of three-dimensional.

In the method for creating a finite element model of a filler compounded rubber according to the invention, preferably, matrix rubber model is obtained by discretizing a space that comprises a first space in which the matrix rubber occupies, a second space in which the filler occupies and a third space in which the interface layer occupies, and the model-embedded step comprises the step of defining a constraint condition between the interface layer model and the matrix rubber model to the third space.

Advantageous Effects of Invention

According to the invention of claim 1, in the first step and the second step, the respective filler model and matrix rubber model are discretized independently one another. Furthermore, the invention of claim 1 includes the model-embedded step where the matrix rubber model and the filler model are overlapped one another without considering the sharing of each node of the models, and the constraint condition is given to at least a boundary between the filler model and the matrix rubber model to define the filler compounded rubber model.

Thus, according to the invention of claim 1, it is possible to define the filler model and the matrix rubber model by discretizing the filler and the matrix rubber using an element having a size and a shape which are suitable for shapes and accuracy requirements thereof. Accordingly, it is possible to define the filler model discretized using a smaller element as well as the matrix rubber model discretized using a larger and simplified element, for example. In such an embodiment, it may be achieved reduction of calculation cost due to the matrix rubber model while maintaining calculation accuracy due to the filler model having a more detailed shape.

The invention according to claim 7 includes the third step of defining the interface layer model obtained by modeling at least one interface layer surrounding the filler independently of the filler model and the matrix rubber model. The third step includes a step of discretizing the interface layer using a finite number of elements. The model-embedded step includes a step of overlapping the interface layer model in the matrix rubber model without considering shearing nodes of the respective models.

According to the invention of claim 7, it is possible to define the filler model, the matrix rubber model and the interface layer model by discretizing the filler, the matrix rubber and the interface layer respectively using an element having a size and a shape which are suitable for shapes and accuracy requirements thereof. Accordingly, it is possible to define the filler model and the interface layer model discretized using a smaller element, while discretizing the matrix rubber model using a larger and simplified element, for example. In such an embodiment, it may be achieved the suppression of calculation cost due to the matrix rubber model while maintaining calculation accuracy due to the filler model and the interface layer model having a more detailed shape.

BRIEF DESCRIPTION OF DRAWINGS

FIG. 5 is a plan view of a visualized matrix rubber model.

Figure 1:
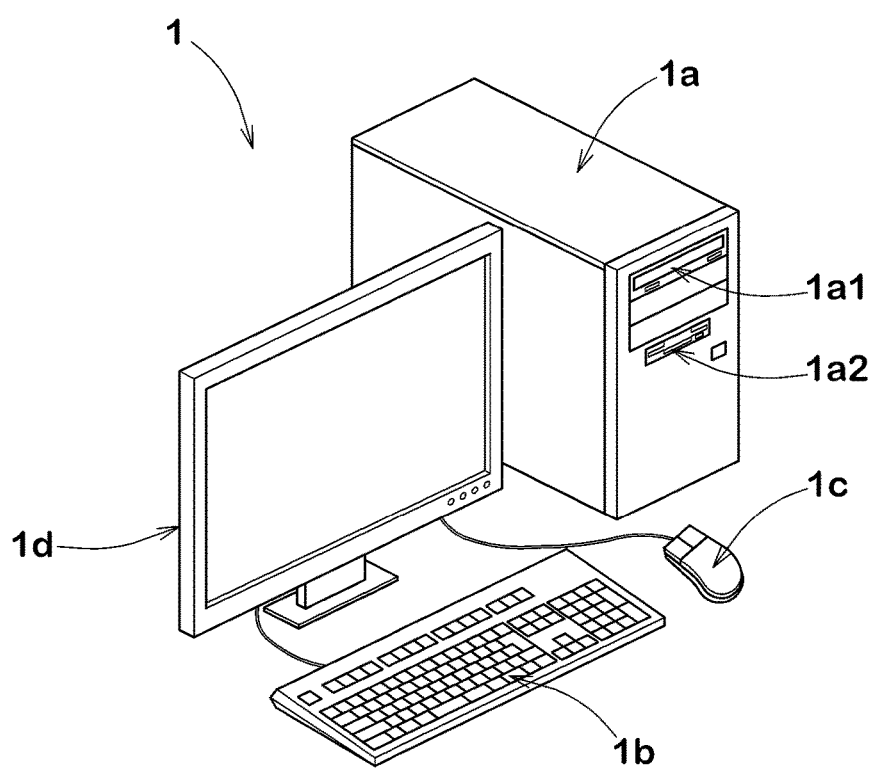
FIG. 1 is a perspective view of a computer that executes a creation method according to the present invention.

REFERENCE SIGNS LIST 2, 25 Filler compounded rubber
2M, 25M Filler compounded rubber model
3 Matrix rubber
3M Matrix rubber model
4 Filler
4M Filler model
28 Interface layer
28M Interface layer model
9 Boundary
32 First boundary
33 Second boundary

DESCRIPTION OF EMBODIMENTS

Hereinafter, an embodiment of the present invention will be explained based on the drawings. A method for creating a finite element model of a filler compounded rubber according to the present invention (hereinafter, it may be simply referred to as "creation method".) is a method for creating a finite element model of the filler compounded rubber (hereinafter, it may be simply referred to as "filler compounded rubber model") which includes a filler dispersed in a matrix rubber with a computer.

FIG. 1 is a perspective view of a computer 1 that executes the creation method according to the present invention. The computer 1 is configured to include a main body 1a, a keyboard 1b, a mouse 1c, and a display unit 1d. The main body 1a, for example, is provided with an arithmetic processing unit (CPU), a ROM, a working memory, a storage device such as a magnetic disk, and disk drive units 1a1 and 1a2. In addition, the storage device is stored a software for performing the creation method of the embodiment and the like (a generic meshing software (e.g., ANSYS, Inc. "ICEM CFD")), in advance.

Figure 2:
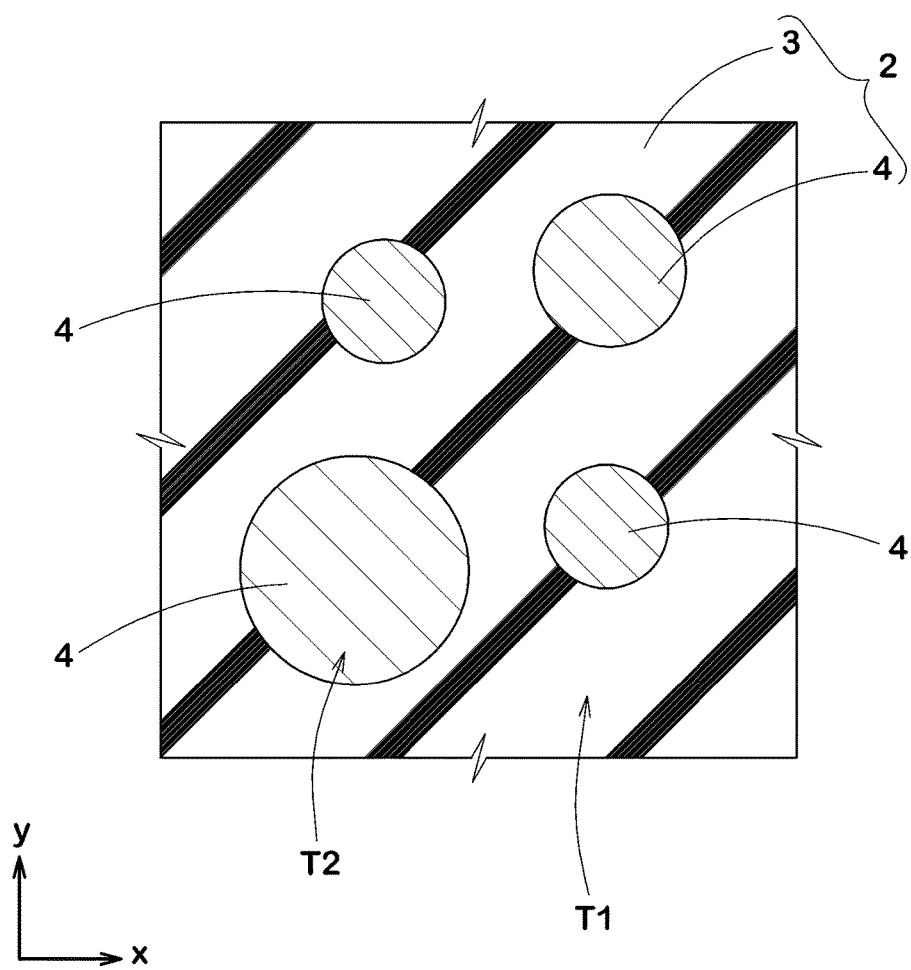
FIG. 2 is a partial enlarged cross-sectional view of a filler compounded rubber.

FIG. 2 is a partial enlarged cross-sectional view of an example of a filler compounded rubber 2 in accordance with the present embodiment. The filler compounded rubber 2 includes a matrix rubber 3 constituting the major part of the rubber and a filler 4 of a substantially circular particle disposed therein. The filler 4 is typically a carbon black, silica and other fillers may be used either alone or in combination with others.

In this embodiment, the finite element model is created based on the filler compounded rubber 2. The finite element model may also be called as a mesh model or the like. The finite element model is created using the computer 1, and then is stored in the computer 1. The computer 1 executes a numerical simulation using the finite element model. In the numerical simulation, various conditions are given to the finite element model, a physical quantity such as displacement or stress of the finite element model of that time is calculated by the computer 1.

In the following embodiments, although an example defined in the two-dimensional coordinate system of x-y will be explained. However, the present invention can be applied to three-dimensional model in the same manner.

Figure 3:
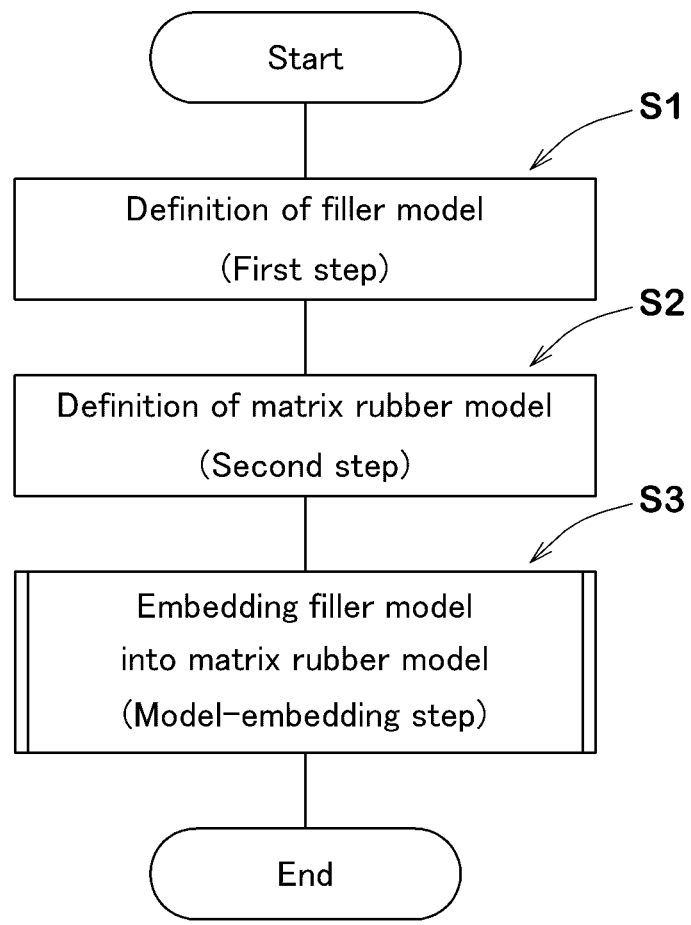
FIG. 3 is a flowchart illustrating an embodiment of a processing procedure of a method for creating a finite element model according to the present embodiment.

FIG. 3 is a flowchart illustrating an embodiment of a processing procedure of a method for creating a finite element model according to the present embodiment. This processing procedure is a procedure for creating the finite element model (filler compounded rubber model) of the filler compounded rubber 2 illustrated in FIG. 1.

As illustrated in FIG. 3, in the creation method of the present embodiment, a first step S1 is performed. In the first step S1, a filler model in which the filler 4 is discretized using a finite number of elements is defined.

Figure 4:
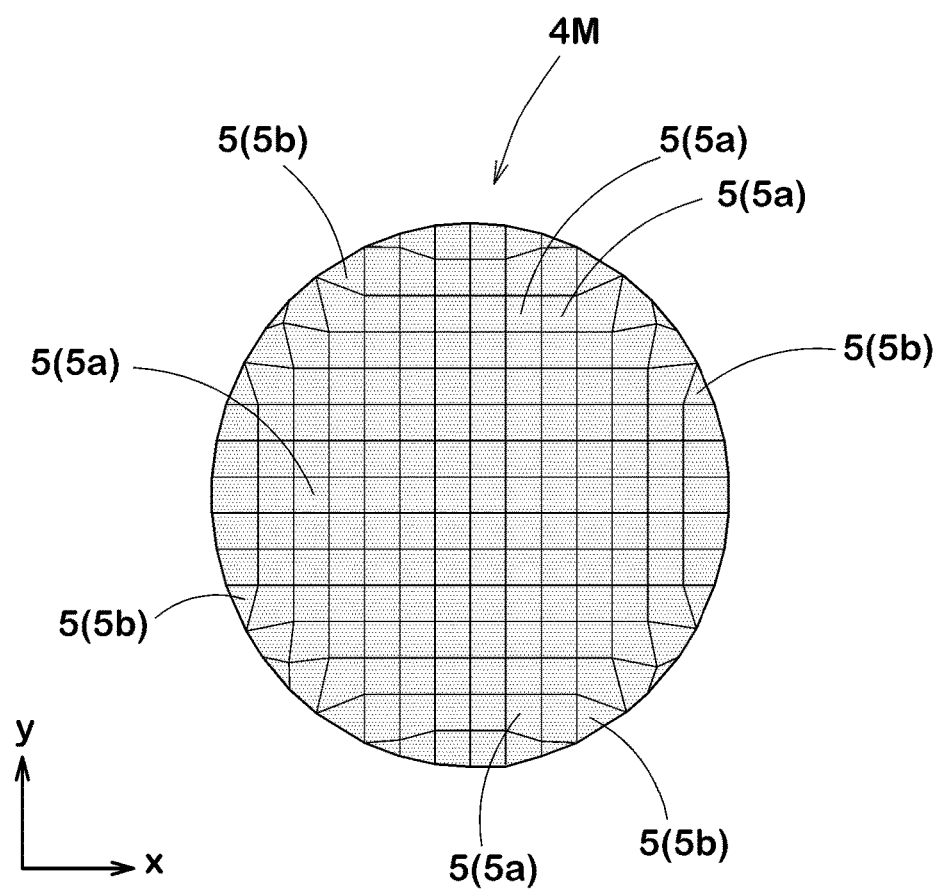
FIG. 4 is a plan view of a visualized filler model.

In FIG. 4, the filler model 4M is visualized. The filler model 4M is one in which a space that is approximately equal to a two-dimensional space in which the filler 4 occupies in the filler compounded rubber 2 is divided (discretized) using a plurality of elements 5. In other words, the filler model 4M is modeled not only the surface of the filler 4 but also the inside of the filler 4.

For the elements 5, when the two-dimensional model of the present embodiment, for example, a quadrilateral element or a triangular element is suitably used. The filler 4 according to the present embodiment has a circular contour. The central portion of the filler model 4M is used a simple quadrilateral elements 5a. The peripheral portion of the filler model 4M is used triangle elements 5b and quadrilateral elements 5b. In this manner, by using elements 5 having different in size and the number of sides, the filler model 4M having a smooth circular contour can be defined.

The coordinate values of nodes and the element numbers of each element 5 of the filler model 4M are stored in the computer 1. In addition, a physical quantity such as elastic modulus and damping factor based on a physical quantity of the filler 4 is inputted in each element 5. The physical quantity is available to calculate deformation of each element 5 (i.e., deformation simulation using the filler compounded rubber model 2M).

Then, in the creation method of the present embodiment, as illustrated in FIG. 3, a second step S2 is performed. In the second step S2, a matrix rubber model 3M is defined. Alternatively, the second step S1 may be performed before the first step S1. Furthermore, the first step S1 and second step S2 may be performed in parallel.

In FIG. 5, the matrix rubber model 3M is visualized. The matrix rubber model 3M is defined by being discretized a space in which at least the matrix rubber 3 occupies in the filler compounded rubber 2 using a finite number of elements 6. In a preferred embodiment, in the second step, a total space of the first space T1 in which the matrix rubber 3 occupies and a second space T2 in which the filler 4 occupies is discretized as the matrix rubber model 3M. That is, according to the present embodiment, the entire region of the filler compounded rubber to be analyzed is discretized by elements 6.

For the elements 6, when the two-dimensional model of the present embodiment, for example, a quadrilateral element or a triangular element is suitably used. Since the matrix rubber model 3M of the present embodiment has a rectangular contour shape, only a simple quadrilateral element 6a is used. In a preferred embodiment, as shown in FIG. 5, the elements 6 of the matrix rubber model 3M are all set to the same size. In another preferred embodiment, the elements 6 of the matrix rubber model 3M may be set larger than or the same as the size of the elements 5 of the filler model 4M (illustrated in FIG. 4). Thus, the matrix rubber model 3M can easily be created in less number of elements than the filler model 4M.

If necessary, the matrix rubber model 3M may be varied the length of the elements 6 in the x-direction or the y-direction. For example, when it is previously understood that a portion to be analyzed is deformed greatly in the x-direction based on the rule of thumb, the length of the element 6 in the x-direction may preferably be set smaller than the length in the y-direction.

The matrix rubber model 3M is defined independently of the filler model 4M. Here, the expression "be defined independently" means that the respective matrix rubber model 3M and filler model 4M are uniquely defined without being associated with one other. For example, nodes of the matrix rubber model 3M may be defined at any positions without sharing the nodes of the filler model 4M.

Thus, in the present embodiment, the matrix rubber 3 and the filler 4 can be discretized elements of size or shape appropriate for each. In a preferred embodiment, by discretizing the filler 4 using a smaller element 5, it is possible to define a filler model 4M that may reproduce outline or shape of the filler 4 accurately. Therefore it is possible to maintain the calculation accuracy.

In another preferred embodiment, the matrix rubber 3 is discretized using a larger element with a simple shape. Since the matrix rubber model 3M is defined with a small number of elements, it is possible to reduce the computational cost. Thus, it is possible to maintain the calculation accuracy while reducing the calculation cost by setting in different size the elements 6 of the matrix rubber model 3M and the elements 5 of the filler models 4M.

The coordinate values of nodes and the element numbers of each element 6 of the matrix model 3M are stored in the computer 1. In addition, a physical quantity such as elastic modulus and damping factor based on a physical quantity of the matrix rubber 3 is inputted in each element 6. The physical quantity is available to calculate deformation of each element 6 (i.e., deformation simulation using the filler compounded rubber model 2M).

Figure 6:
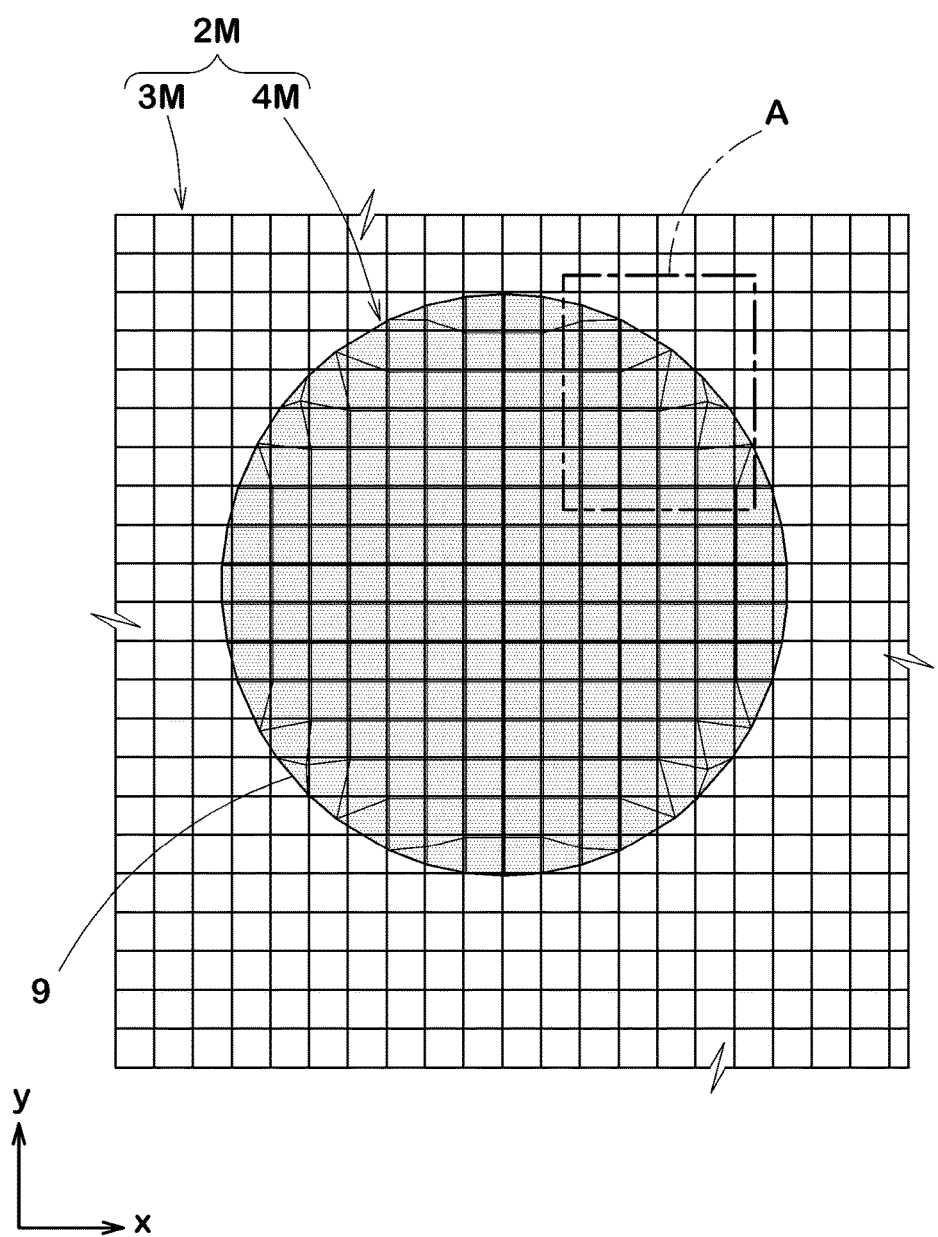
FIG. 6 is a plan view of a filler compounded rubber model of the present embodiment.
Figure 7:
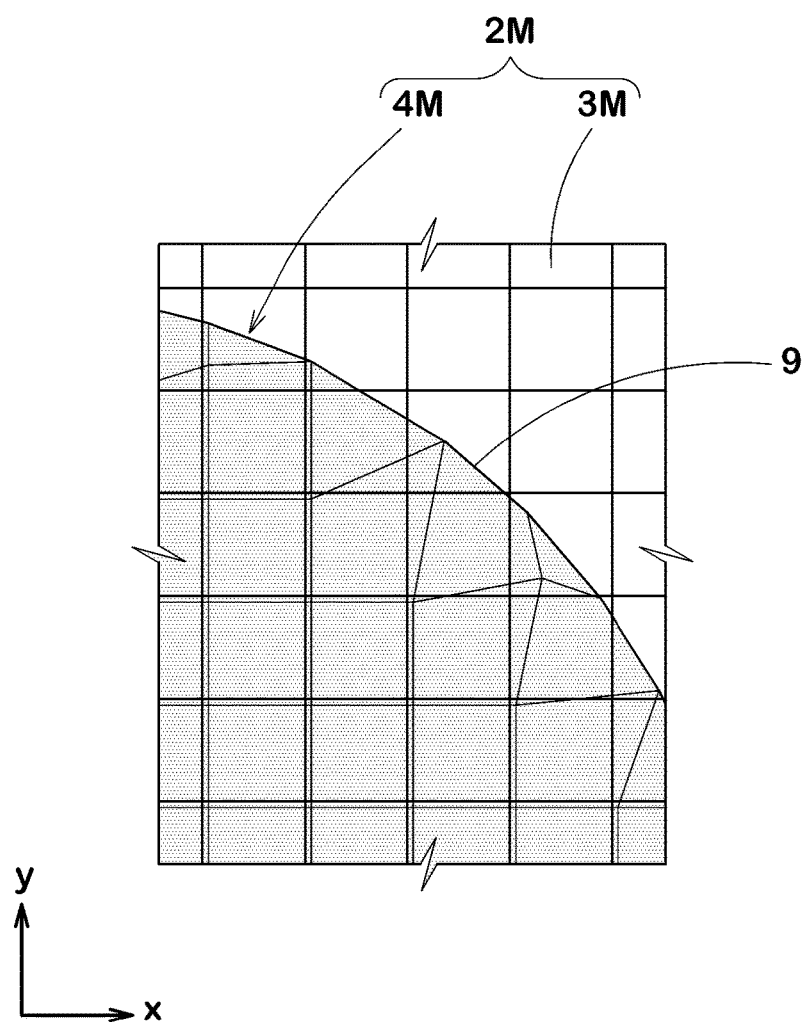
FIG. 7 is an enlarged view of a portion A of FIG. 6.
Figure 8:
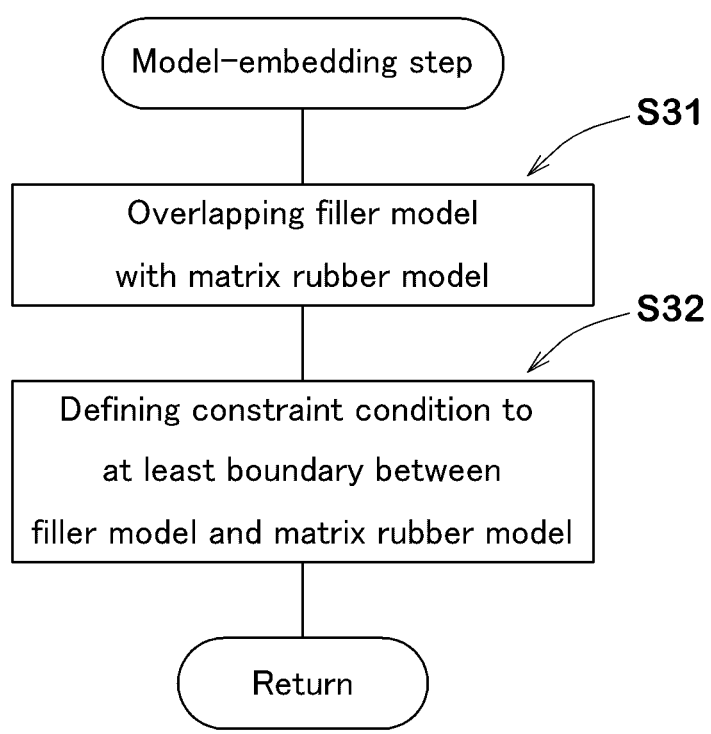
FIG. 8 is a flowchart illustrating an embodiment of a processing procedure of model-embedded step according to the present embodiment.

Then, the creation method of the present embodiment, as shown in FIG. 3, the model-embedded step S3 is performed. In the model-embedded step S3, the filler-model 4M is embedded in the matrix rubber model 3M as illustrated in FIG. 6 and FIG. 7 which is an enlarged view of the portion A of FIG. 6. FIG. 8 is a flowchart illustrating an example of a processing procedure of the model-embedded step S3 of the present embodiment.

In model-embedded step S3 according to the present embodiment, firstly, the matrix rubber model 3M and the filler model 4M are overlapped one another without considering sharing of the respective nodes of the filler model 4M and the matrix rubber model 3M (step S31). That is, in the model-embedded step S3, mutual two or more models are allowed to overlap one another. The position of the filler model 4M to the matrix rubber model 3M is determined based on the filler compounded rubber 2 to be analyzed.

In the model-embedded step S3 according to the present embodiment, then, a constraint condition to prohibit the relative deformation is given to at least a boundary (to the boundary in this embodiment) between the filler model and the matrix rubber model (step S32). With this, the filler compounded rubber model 2M is defined in the computer 1.

Figure 9:
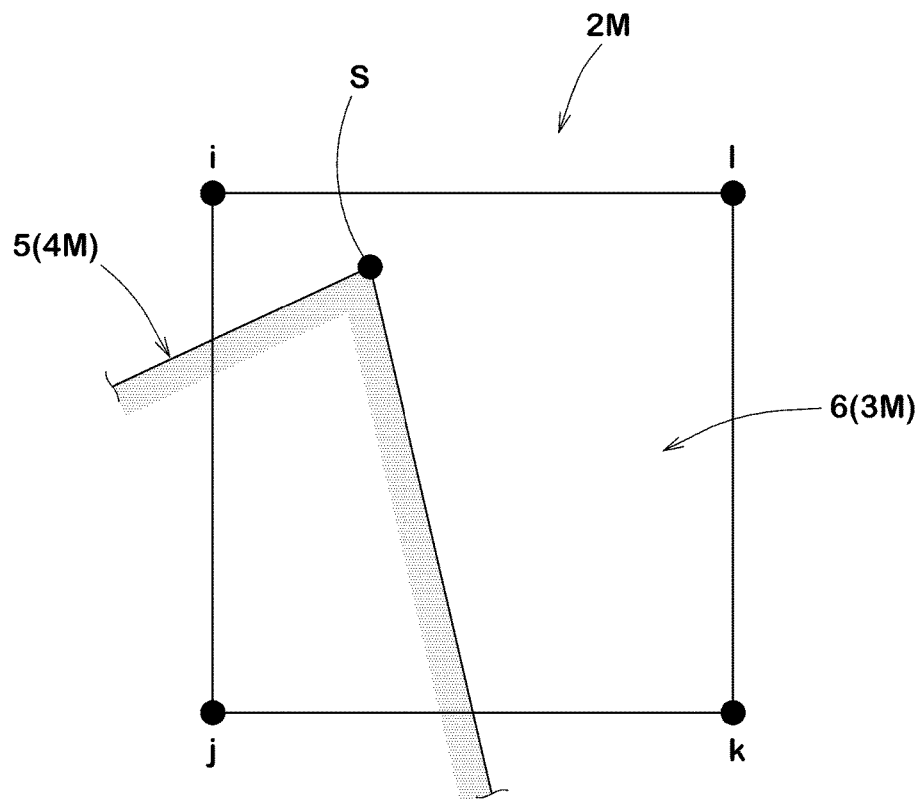
FIG. 9 is a diagram illustrating a constraint condition of a boundary.

The constraint condition is a condition for constraining a translational degrees of freedom between nodes of the filler model 4M and the matrix rubber model 3M. The constraint condition is stored in the computer 1. FIG. 9 is a diagram illustrating a part of the visualized filler compounded rubber model 2M.

In FIG. 9, one of the elements 6 is illustrated as the matrix rubber model 3M. The element 6 includes a node i, j, k and l. In addition, in FIG. 9, the element 5 of filler model 4M which is embedded (overlapped) within the matrix rubber model 3M is illustrated. The node S of the element 5 of the filler model 4M is located in the interior of the element 6 of the matrix rubber model 3M.

In step S32, first, it is determined whether the node of the elements 5 of the filler models 4M is present within the region of the element 6 of the matrix rubber model 3M. This determination is performed for all the elements 6 of the matrix rubber model 3M.

Then, in step S32, when it is determined that the node S of the elements 5 of the filler model 4M is present in the element 6 of the matrix rubber model 3M, the weighting factor of the node S is determined based on the geometry position of the node S to the element 6 of the matrix rubber model 3M. The weighting factor has a relationship of inversely proportional to distances from the node of the element 5 of the filler model 4M to each node i, j, k and l of the element 6 of the matrix rubber model 3M that surrounds the node S. The closer the node S is to the node i, j, k or l, the more strongly the node S is restricted. In this example, the node S is bound strongly to the node i. Thus, the degree of freedom of the node S (translational degrees of freedom) is restrained based on the weighting factor.

The weighting factor is calculated with respect to all the nodes S of the elements 5 of the filler model 4M. Thus, relative movement between the matrix rubber model 3M and the filler model 3M can be restrained at the boundary 9 between the matrix rubber model 3M and the filler model 3M.

As described above, in the creation method of the present embodiment, since the matrix rubber model 3M and the filler model 4M are defined independently each other, it is unnecessary to consider not only the sizes but also sharing the respective nodes of elements 5 and 6. Therefore, time and effort of modeling is reduced. Furthermore, the creation method of the present embodiment can be reproduced the contours of the filler 4 in precisely to the simulation while preventing an increase in the number of elements. Furthermore, since the constraint condition is given to the boundary 9 between the matrix rubber model 3M and the filler models 4M which are defined independently, even if no node is shared, force and displacement is accurately transmitted through the boundary 9. Thus, the creation method of the present embodiment prevents reduction of calculation precision.

In step S32 of the present embodiment, it has been explained that the constraint condition is given to only the boundary portion 9 between the matrix rubber model 3M and the filler model 4M. However, the present invention is not limited to such an embodiment. In step 32, for example, the constraint condition between the filler model 4M and the matrix rubber model 3M may be defined in a region corresponding to the second space T2 (shown in FIG. 2) in which the filler 4 occupies. Thus, the relative movement between the filler model 4M and the matrix rubber model 4M can be constrained more strongly, and it may help to improve the calculation accuracy.

Although the filler compounded rubber model 2M according to the present embodiment has been exemplified to be created as a two-dimensional model, it may be created as a three-dimensional model. In this case, the matrix rubber model 3M and the filler model 4M, for example, are preferably discretized using a three-dimensional elements composed of a hexahedral element or a tetrahedral elements, etc. (not shown).

In the creation method according to the present embodiment, it has been explained that the total space of the first space T1 in which the matrix rubber 3 occupies and the second space T2 in which the filler 4 occupies, as shown in FIG. 2, is discretized as the matrix rubber model 3M. However, the present invention is not limited to such an embodiment. For example, a total space of the first space T1 and a part of the second space T2 in which the surface of the filler model overlaps with the first space may be discretized as the matrix rubber model 3M. Such a matrix rubber model 3M may reduce the number of elements 6 as compared to a matrix rubber model 3m which is formed by discretizing the total space of the first space T1 and the second space T2, and therefore computational cost can be reduced.

In this embodiment, although a solid filler model 4 in which the inside of the filler is also discretized using a finite number of elements 5 has been explained, it is not limited to such an embodiment. For example, a hollow filler model 4M (not shown) in which only the surface of the filler 4 is discretized using a finite number of elements 5 may be available. Such a hollow filler model 4M is possible to reduce the number of elements 5 as compared with the solid filler model 4M, thereby reducing the computation time.

Figure 10A:
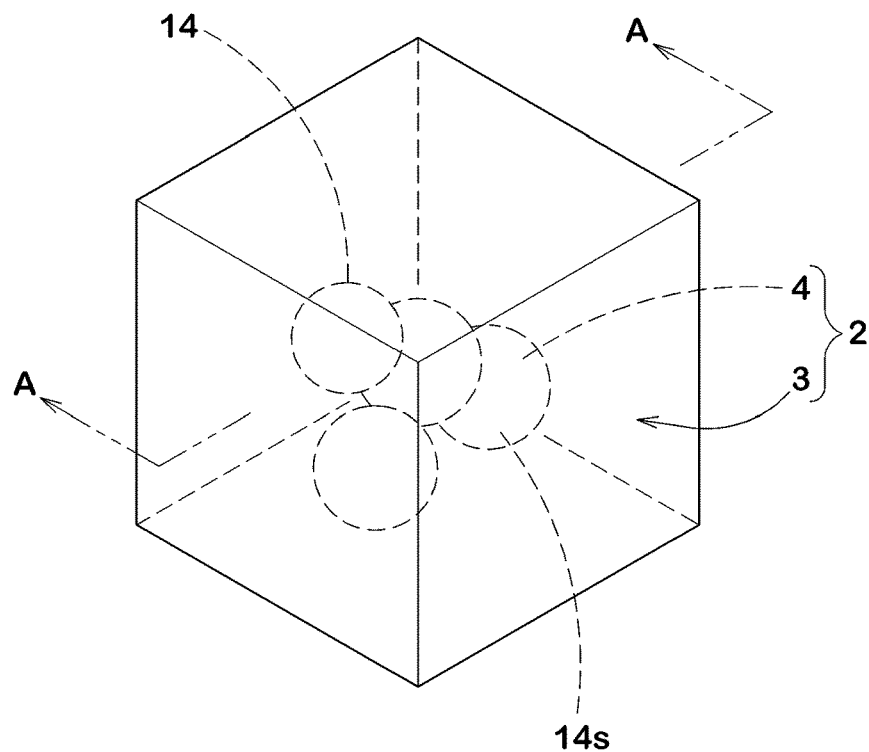
FIG. 10A is a partial perspective view illustrating an example of the filler compounded rubber of the present embodiment.
Figure 10B:
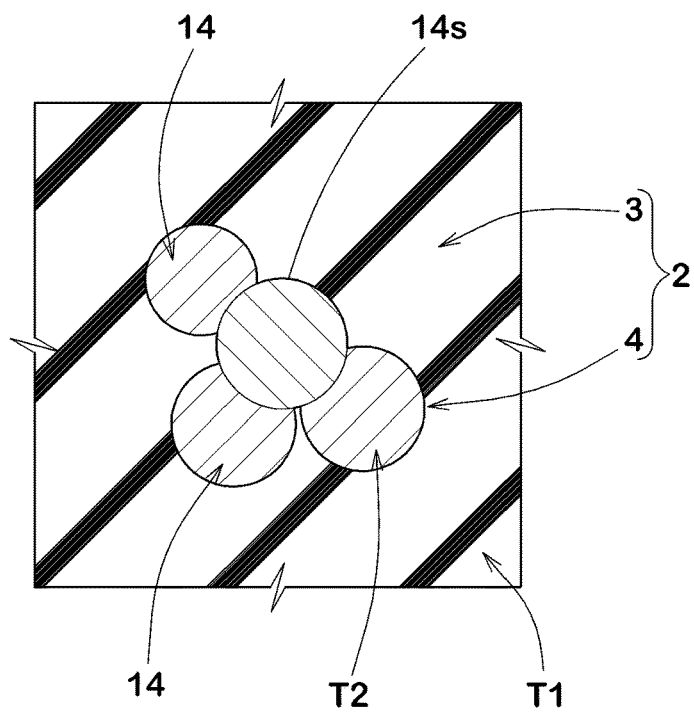
FIG. 10B is a cross-sectional view taken along lines A-A of FIG. 10A.

In the creation method according to the present embodiment, it has been exemplified that the filler model 4 is defined by discretizing each filler 4 of the filler compounded rubber 2, but it is not limited to such an embodiment. FIG. 10A is a partial perspective view illustrating another example of the filler compounded rubber 2 of the present embodiment, and FIG. 10B is a cross-sectional view taken along lines A-A of FIG. 10A.

The filler 4 according to the present embodiment includes an aggregate of a plurality of primary particles 14. Such a filler 4 has a complicated surface shape thereof owing to the aggregate of a plurality of primary particles 14. Therefore, it is difficult to discretized the filler 4 along the surface shape thereof. The creation method of the present embodiment, the filler model 4M is defined based on each primary particle model 14M in which each primary particle 14 is modeled.

Figure 11:
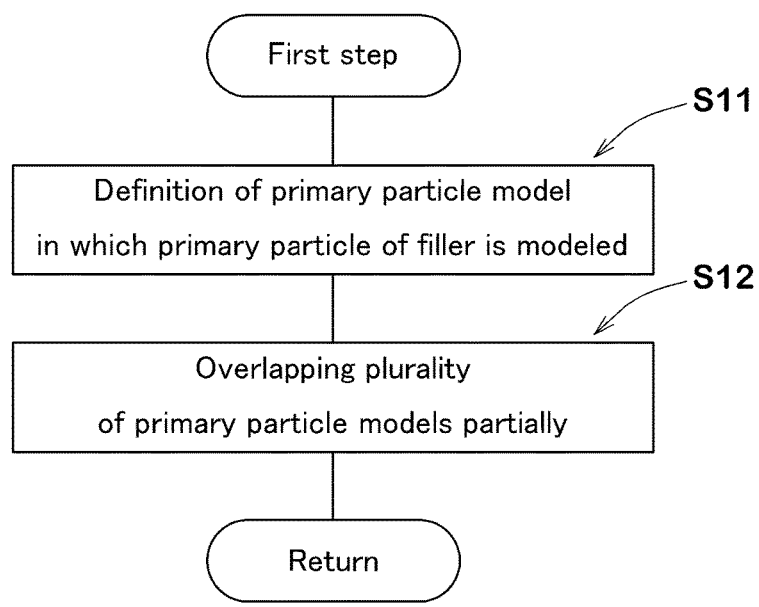
FIG. 11 is a flowchart illustrating an example of a processing procedure of the first step (step of defining a filler model).
Figure 12A:
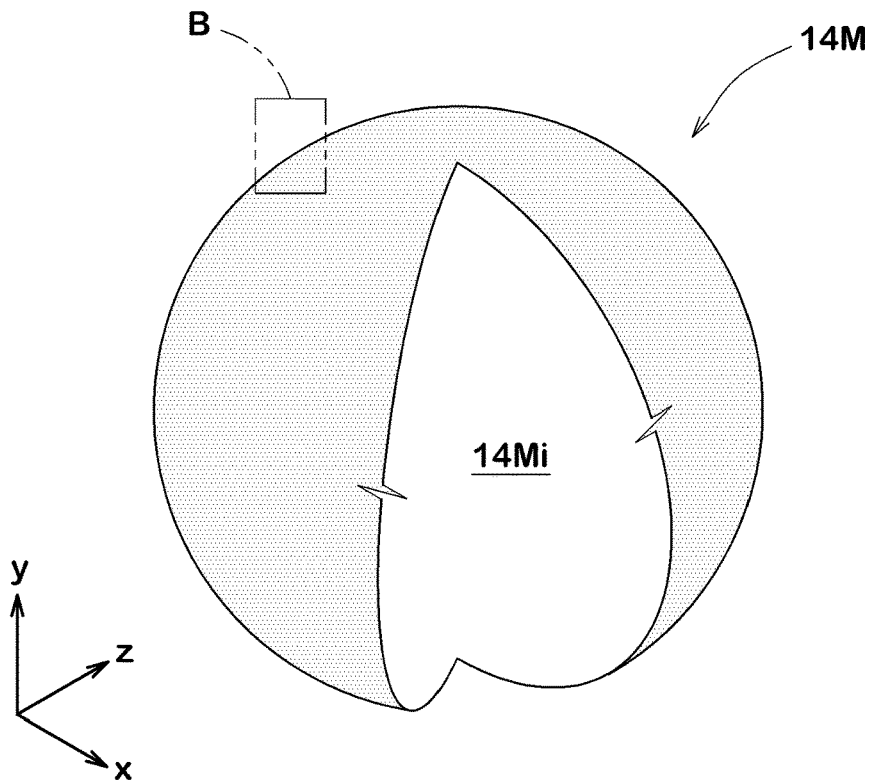
FIG. 12A is a perspective view illustrating a visualized primary particle model.
Figure 12B:
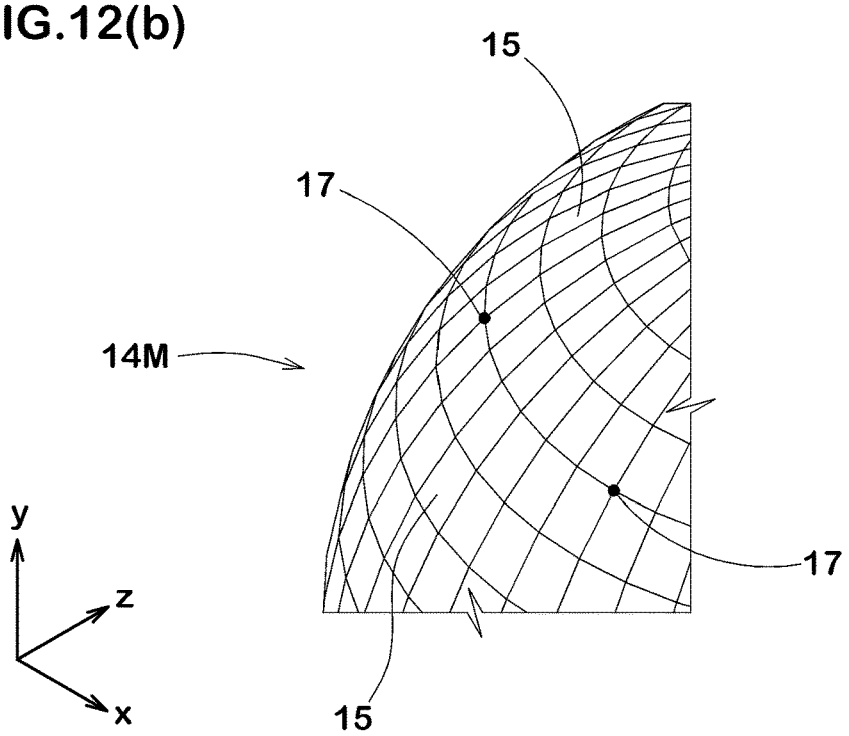
FIG. 12B is an enlarged view of a portion B of FIG. 12A.

The processing procedure of the creation method of the present embodiment is carried out in the same procedure as the prior embodiment shown in FIG. 3. Furthermore, the filler compounded rubber model 2M in this embodiment is created as a three-dimensional model. FIG. 11 is a flowchart illustrating an example of the processing procedure of the first step S1, FIG. 12A is a perspective view illustrating a visualized primary particle model 14M, and FIG. 12B is an enlarged view of a portion B of FIG. 12A.

In the first step S1 of the present embodiment, each primary particle model 14M is defined by discretizing each primary particle 14 of the filler 4 shown in FIG. 10 using a finite number of elements (step S11). The primary particle model 14M of the present embodiment is one in which only the surface 14s of the primary particle 14 shown in FIG. 10 is divided (discretized) using a finite number of elements 15. Thus, the primary particle model 14M is defined as a hollow shape having a void 14Mi therein.

For the elements 15 in accordance with the three-dimensional model as in the present embodiment, two-dimensional elements (surface elements) are used. The two-dimensional elements 15, for example, quadrilateral or triangular elements are suitably used. In step S11, the surface 14s of the primary particle 14 (shown in FIG. 10) can be discretized using a plurality of elements 15. Such a primary particle model 14M, for example, may reduce the computational cost because the number of elements 15 is small as compared with a solid model in which not only the surface but also the inside of the primary particle are discretized.

In step S11 of the present embodiment, since the two-dimensional elements 15 are used, it can discretize easily the primary particles 14 along the surface 14s having the convex or concave portions (shown in FIG. 2). Thus, it is possible to define a primary particle model 14M that are faithfully reproduced the shape of the surface 14s of the respective primary particles 14. When the unevenness of the surface 14s of the primary particles 14 is large, it is preferable that elements 15 are set to be small.

The primary particle model 14M is defined independently of the matrix rubber model 3M. Thus, the nodes 17 of the primary particle model 14M may be defined at any positions because there is no necessity to share with the nodes 12 of the matrix rubber model 3M (shown in FIG. 15). Accordingly, the primary particle model 14M may represent accurately the surface shape of the filler 4 (shown in FIG. 10).

The lengths of elements 15 of the primary particle model 14M in the x-axis direction, y-axis direction and z-axis direction can be varied as required. As a result, the elements 15 of the primary particle model 14M can be formed in different size to the elements 6 of the matrix rubber model 3M (shown in FIG. 15). Furthermore, it is preferable that a length in each direction of the elements 15 of the primary particle model 14M is set smaller than a length of each direction of the elements 6 of the matrix rubber model 3M. Thus, it is possible that the primary particle model 14M represents the shape of the surface 14s accurately even when the primary particle 14 has large unevenness of the surface 14s shown in FIG. 10, and therefore the calculation accuracy can be maintained.

The coordinate values of nodes 17 and the element numbers of each element 15 of the respective primary particle models 14M are stored in the computer 1. In addition, a physical quantity such as elastic modulus and damping factor based on a physical quantity of the primary particles 14 (shown in FIG. 10) is inputted in each element 15. The physical quantity is available to a deformation simulation using the filler compounded rubber model 2M (shown in FIG. 16).

As described above, since each primary particle model 14M is defined as a hollow shape having a void therein, there is a tendency that the rigidity would be defined smaller as compared to the solid shape model. Thus, it is preferable that the physical quantity to be inputted to each element 15 is set greater than the physical quantity based on the primary particles 14 which is to be set to a solid shape model. With this, it is possible to offer the overall rigidity of each primary particle model 14M close to the physical quantity of the primary particle 14, thereby improving the calculation accuracy.

Figure 13:
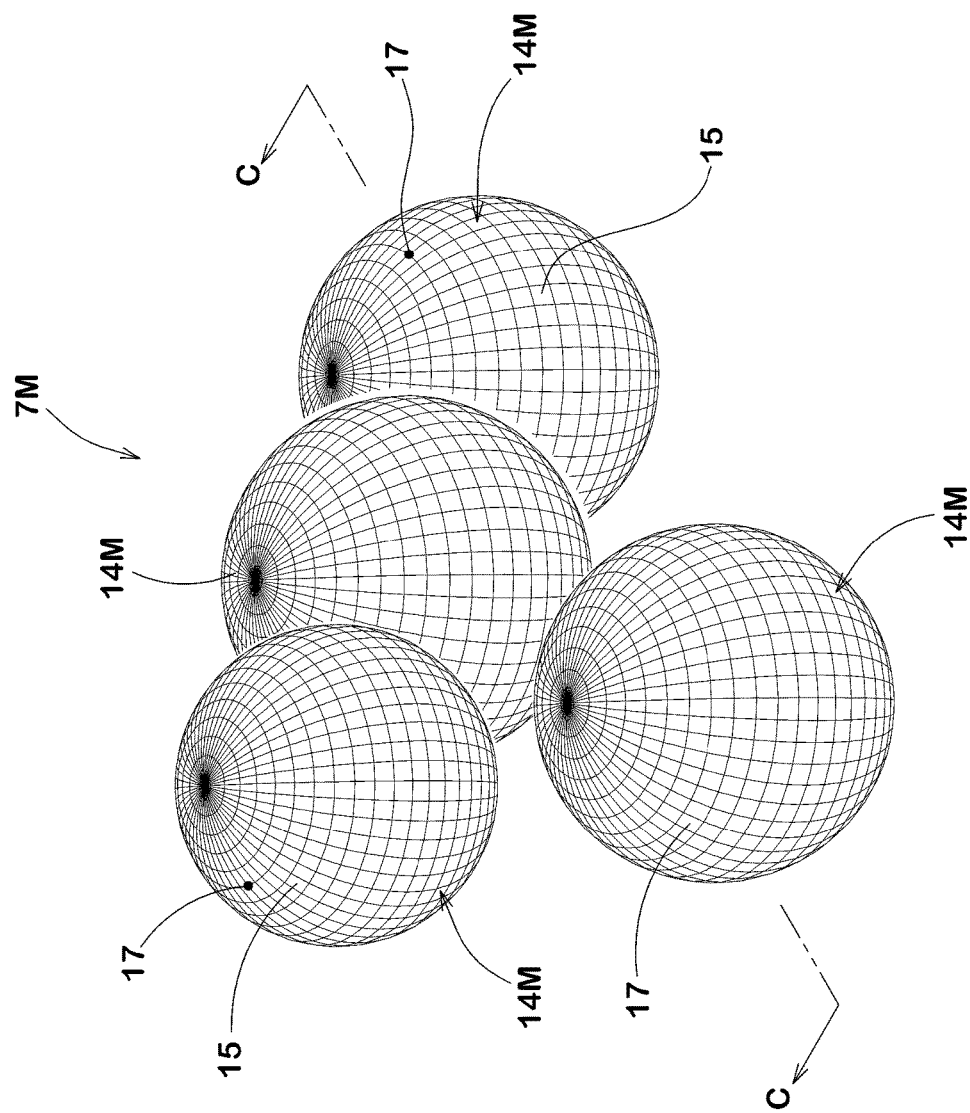
FIG. 13 is a perspective view of a visualized filler model.
Figure 14:
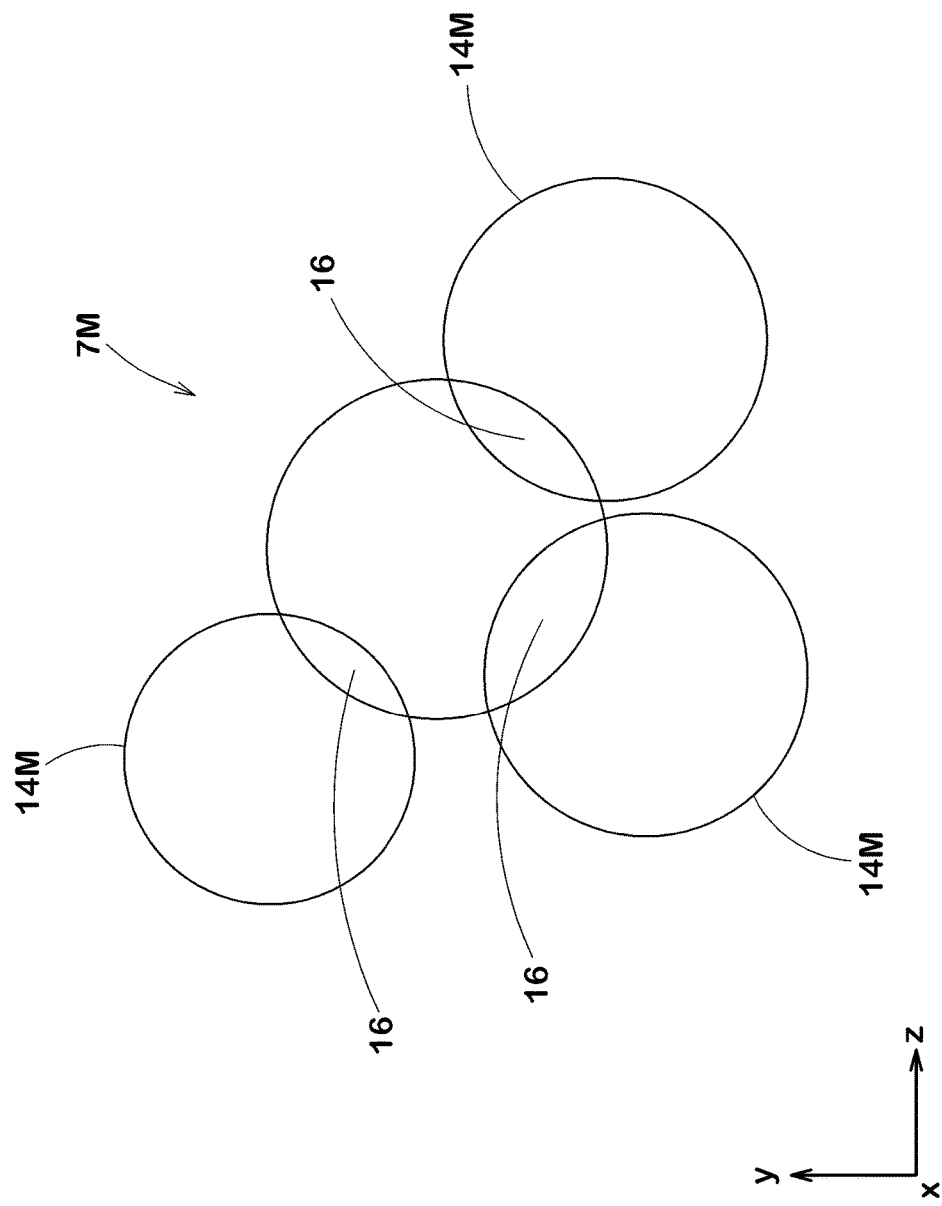
FIG. 14 is a cross-sectional view taken along lines C-C of FIG. 13.

Then, in the first step S1 of the present embodiment, a plurality of primary particle models 14M are partially overlapped (step S12). FIG. 13 is a perspective view of a visualized filler model 7M. FIG. 14 is a cross-sectional view taken along lines C-C of FIG. 13. In FIG. 4, elements 15 of the primary particle models 14M are not illustrated.

In step S12 of the present embodiment, a plurality of primary particle models 14M are set to overlap one another partially without considering sharing of the respective nodes 17 of the elements 15 of the primary particle models 14M. The position of the primary particle models 14M are set based on the filler compounded rubber 2 shown in FIG. 10.

Thus, in step S12, the filler model 4M including an aggregate of a plurality of primary particle models 14M is set.

In step S12, the filler model 4M with a faithful surface shape of the filler 4 shown in FIG. 10B can be easily defined by only overlapping a plurality of primary particle models 14M partially. Accordingly, step S12 of the present embodiment can reduce the creating time of the filler compounded rubber model 2M (shown in FIG. 16). The position information of the primary particle models 14M are stored in the computer 1.

Figure 15:
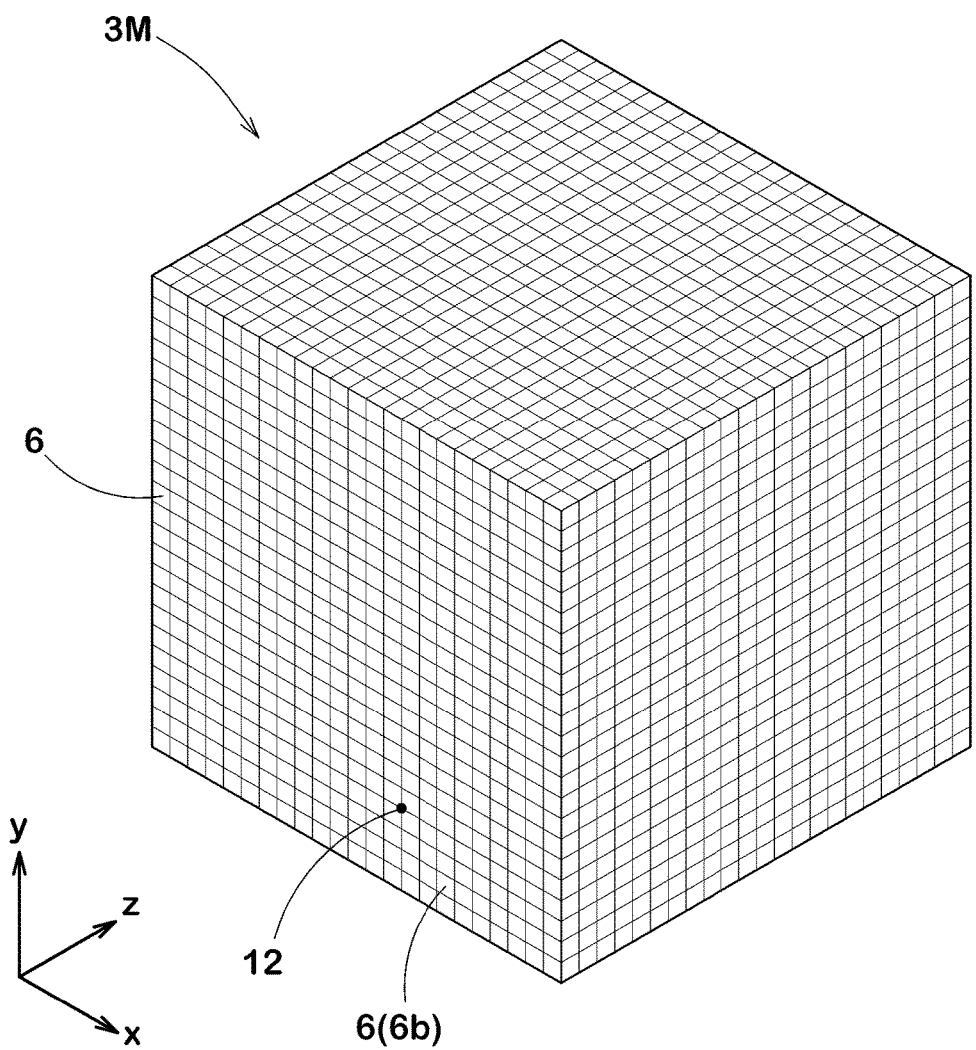
FIG. 15 is a perspective view illustrating a visualized matrix rubber model.

FIG. 15 is a perspective view showing a visualized matrix rubber model. In the second step S2 of the present embodiment, the total space of the first space T1 in which the matrix rubber 3 occupies and the second space T2 in which the filler 4 occupies, shown in FIG. 10B, is discretized using three-dimensional elements 6. As a result, the matrix rubber model 3M is defined. For the three-dimensional elements 6, for example, a hexahedron element or a tetrahedral element is preferably used.

The matrix rubber model 3M according to the present embodiment has a contour formed in a rectangular shape. For the elements 6, only a simple hexahedron elements 6b are used. Furthermore, each element 6 is all set to the same size. In addition, it is preferable that each element 6 is equal to or greater than the elements 15 of the primary particle models 14M. Thus, in the second step S2, the matrix rubber model 3M can be created in less elements.

Lengths of the elements 6 of the matrix rubber model 3M in the x-axis direction, y-axis direction or z-axis direction can be varied as required. For example, when it is previously understood that a portion to be analyzed is deformed greatly in the x-direction based on the rule of thumb, the length of the elements 6 in the x-direction may preferably be set smaller than the length in the y-direction. In such a matrix rubber model 3M, since the number of elements 6 in the x-axis direction is relatively increased, the deformation in the x-axis direction can be calculated accurately.

The coordinate values of nodes 12 and the element numbers of each element 6 of the matrix rubber model 3M are stored in the computer 1. In addition, a physical quantity such as elastic modulus and damping factor based on the physical quantity of the matrix rubber 3 is inputted in each element 6. The physical quantity is available to calculate deformation simulation using the filler compounded rubber model 2M.

Figure 16:
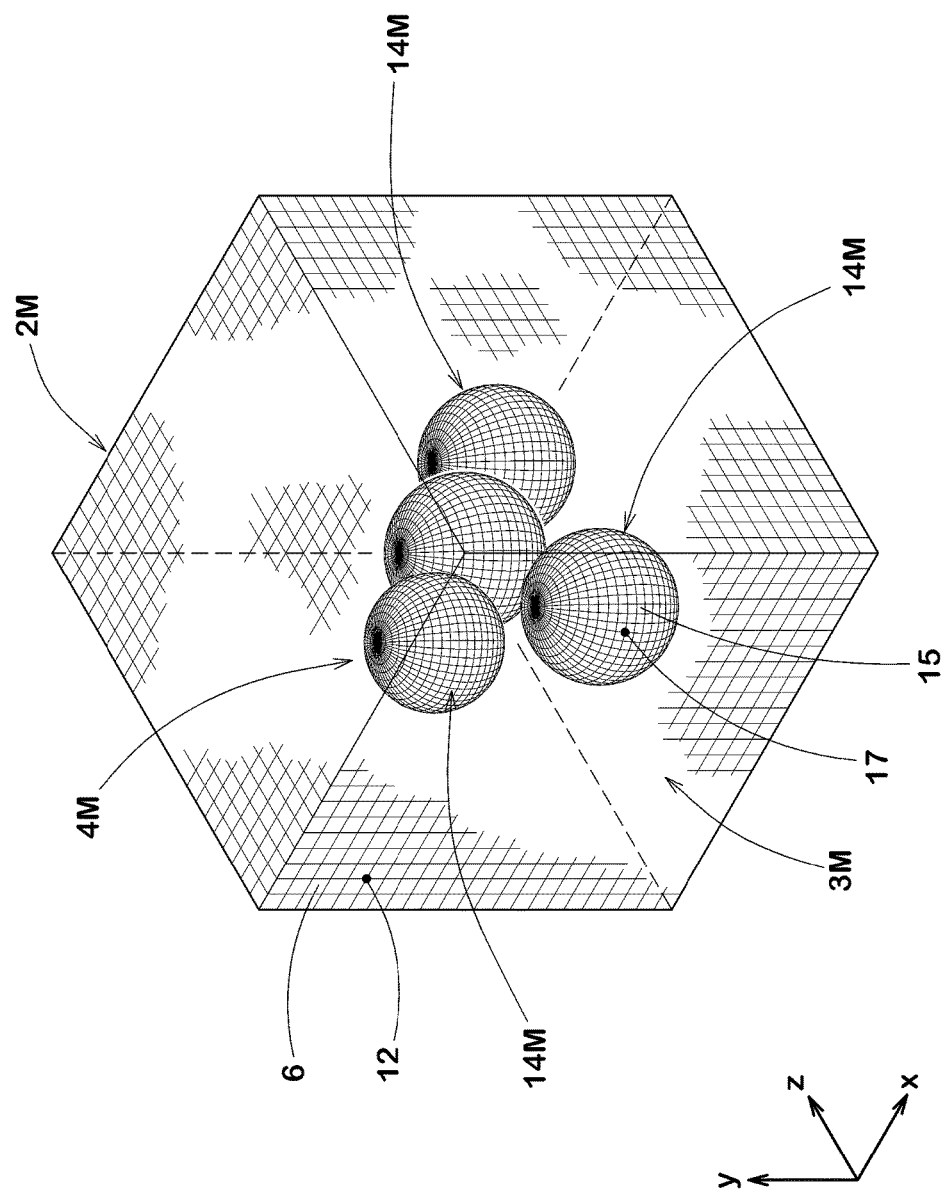
FIG. 16 is a perspective view illustrating an example of a visualized filler compounded rubber model.

FIG. 16 is a perspective view illustrating an example of a visualized filler compounded rubber model. In FIG. 16, some of the elements 6 of the matrix rubber model 3M is omitted.

In model-embedded step S3 of the present embodiment, similarly to the model-embedded step S3 of the previous embodiment shown in FIG. 8, the matrix rubber model 3M and the filler model 4M are arranged so as to overlap without considering sharing of the respective nodes of the filler model and the matrix rubber model (step S31). In step S31 according to the present embodiment, as shown in FIG. 16, the filler model 4M is positioned inside the matrix rubber model 3M without considering sharing between the nodes 12 of the elements 5 of the matrix rubber model 3M and the nodes 17 of the elements 15 of the primary particle models 14M. That is, in step S31, the mutual two or more models are allowed to overlap. The position of the filler model 4M (primary particle models 14M) to the matrix rubber model 3M is determined based on the filler compounded rubber 2 to be analyzed. The number of primary particle models 14M are identical to the number of primary particles 14 (shown in FIG. 2).

Figure 17:
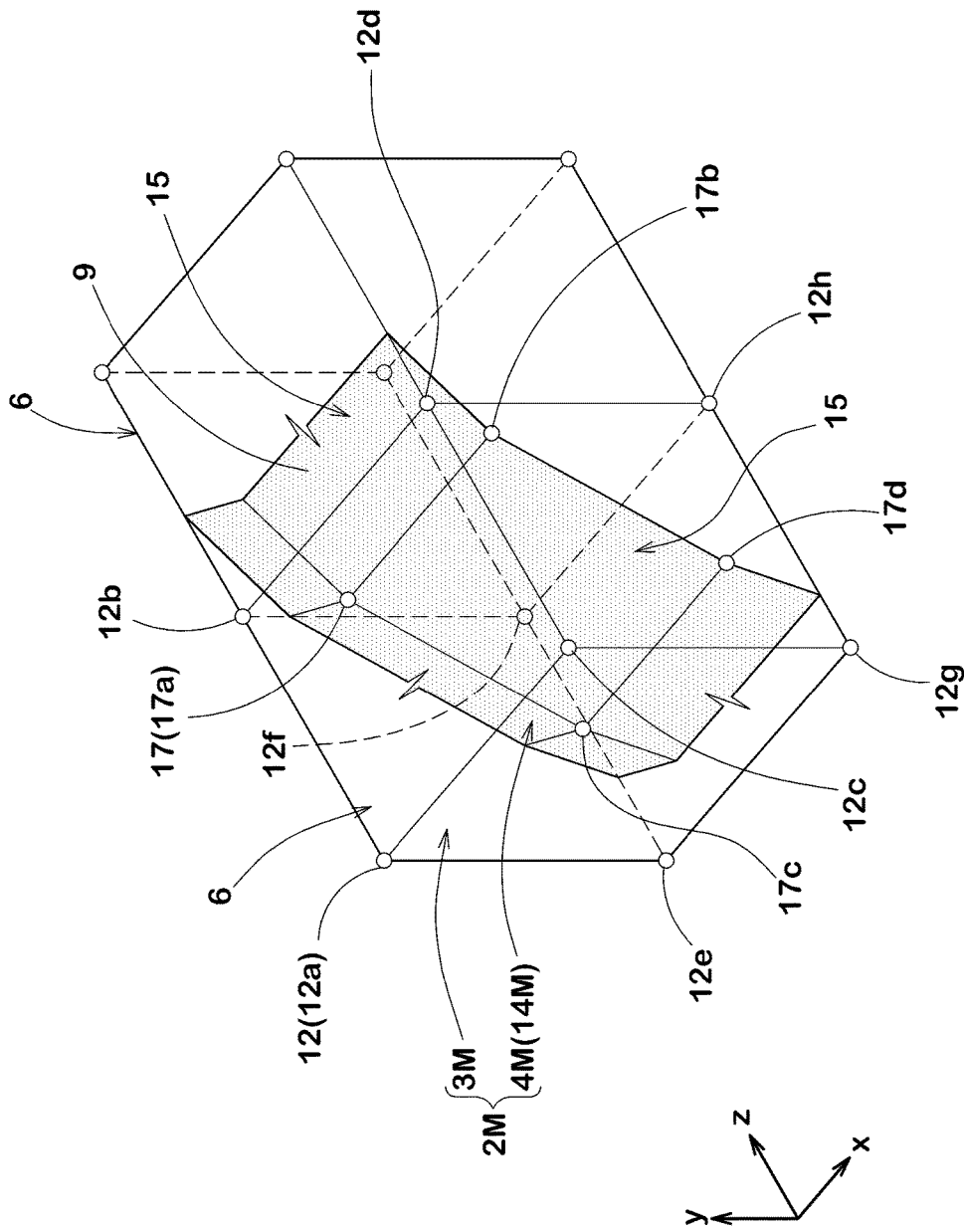
FIG. 17 is a partial enlarged view of the filler compounded rubber model.

Then, in the model-embedded step S3 of the present embodiment, a constraint condition is given to at least the boundary between the filler model 4M and the matrix rubber model 3M (step S32). FIG. 17 is a partial enlarged view of the filler compounded rubber model 2M. The constraint condition in the present embodiment, as with the previous embodiment, is defined to the boundary 9 between each primary particle model 14M and the matrix rubber model 3M (shown in FIG. 7). The constraint condition in the present embodiment, as with the previous embodiment, is a condition for constraining the translational degree of freedom of a node 12 of the matrix rubber element 3M and a node 17 of the primary particle model 14M. Such a constraint condition is calculated by the computer 1.

FIG. 17 illustrates two elements 6 and 6 as the matrix rubber model 3M. Each element 6 includes nodes 12a, 12b, 12c, 12d, 12e, 12f, 12g and 12h. Furthermore, an element 15 of the primary particle model 14M is overlapped with one of the elements 6 of the matrix rubber model 3M. The elements 15 include nodes 17a, 17b, 17c and 17d. These nodes 17a to 17d are located inside one of the elements 6 of the matrix rubber model 3M.

In step S32, first, it is determines whether each node 17a to 17d of the element 15 of the primary particle model 14M is present in the region of the element 6 of the matrix rubber model 3M. The determination is performed for all the elements 6 of the matrix rubber model 3M.

Then, in step S32, when it is determined that one of the nodes 17a to 17d of the element 15 of the primary particle model 14M is present in the elements 6 of the matrix rubber model 3M, the weighting factors of the concerned node 17a to 17d is determined based on the geometry positions of the concerned node 17a to 17d to the element 6 of the matrix rubber model 3M.

The weighting factors, as with the previous embodiment, has a relationship of inversely proportional to distances from the concerned node 17a to 17d of the element 15 of the primary particle model 14M to each node 12a to 12d of the element 6 of the matrix rubber model 3M that surrounds the node thereof. The concerned node 17a to 17d of the element 15 of the primary particle model 14M is constrained strongly closer to each node 12a to 12f of the element 6 of the matrix rubber model 3M. For example, the node 17b of the element 15 of the primary particle model 14M is most strongly constrained to the node 12d of the element 6 of matrix rubber model 3M. Thus, the degree of freedom of all the nodes 17a to 17d (translational degrees of freedom) is restrained based on weighting factors.

In the model-embedded step S3, by defining the constraint condition between the matrix rubber model 3M and filler model 4M, the filler compounded rubber model 2M (shown in FIG. 16) can be set.

Although the nodes 12 of the elements 6 of the matrix rubber model 3M are not shared with the nodes 17 of the elements 15 of the primary particle model 14M in the filler compounded rubber model 2M, force and displacement is accurately transmitted through the boundary 9 because the constraint condition is given to the boundary 9 between the matrix rubber model 3M and the primary particle models 14M. Accordingly, the filler compounded rubber model 2M of the present embodiment may prevent deterioration of the calculation accuracy in a deformation simulation. The filler compounded rubber model 2M is stored in the computer 1.

It is preferable that the weighting factor is calculated for all the nodes 17a to 17d, which include nodes 17 of elements 15 located within an overlapped region 16 (shown in FIG. 14) between the primary particle models 14M and 14M, of each element 15 of the primary particle models 14M. Thus, since the constraint condition is given to each element 17 of the primary particle models 14M without considering the presence of other primary particle models 14M, relative movement between each primary particle model 14M and the matrix rubber model 3M tightly constrained. Accordingly, the filler compounded rubber model 2M may maintain the surface shape of the filler model 4M and may increase the calculation accuracy.

In the creation method according to the present embodiment, it has been exemplified an aspect where the filler model 4 is previously modeled by overlapping the primary particle models 14M partially and then is positioned inside the matrix rubber model 3M. However, the present invention is not limited to the aspect. For example, it may be possible to be set the filler model 4M including an aggregate of a plurality of primary particles 14M by arranging the respective primary particle models 14M directly within the matrix rubber model 3M. Furthermore, in the present embodiment, it has been exemplified an aspect where one filler model 4M is disposed in the matrix rubber model 3M, but the present invention is not limited to such an aspect. For example, a plurality of filler models 4M may be arranged dispersely in the interior of the matrix rubber model 3M.

It has been exemplified that the filler compounded rubber model 2M according to the present embodiment is modeled as a three-dimensional model, but it may be created as a two-dimensional model. In this case, it is preferable that the filler model 4M is such that only the surface 4s of the filler 4 is discretized using a line element (not shown) of one-dimension. Furthermore, it is preferable that the matrix rubber model 3M is created by discretizing using a quadrilateral element or a triangular element (not shown).

Figure 18:
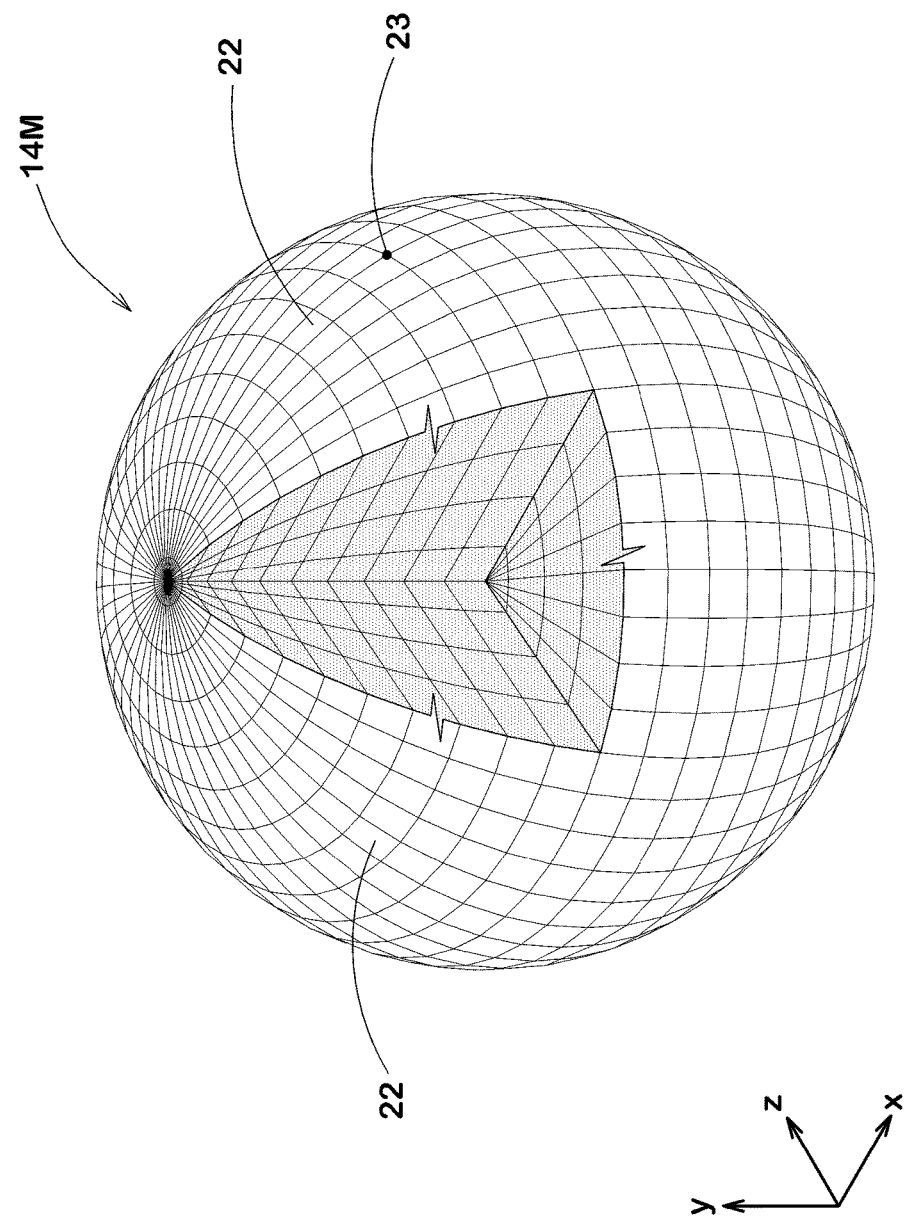
FIG. 18 is a perspective view illustrating an example of the primary particle model in accordance with another embodiment of the present invention.

In the creation method of the present embodiment, it has been exemplified an aspect where each primary particle model 14M is set by discretizing only the surface 14s of each primary particle 14 using two-dimensional elements 15. However, the present invention is not limited to such an aspect. FIG. 18 is a perspective view of a primary particle model 14M in accordance with another embodiment of the present invention.

The primary particle model 14M, as with the matrix rubber model 3M, may be created by discretizing a primary particle 14 using three-dimensional elements 22. For the three-dimensional elements 22, as with the elements 6 of the matrix rubber model 3M, for example, a hexahedron element or a tetrahedral elements are preferably used. Thus, the primary particle model 14M is set as a solid model which is modeled not only the surface 14s of the primary particle 14 but also the inside of the primary particle 14. Such a solid primary particle model 14M may be set a large rigidity as compared with the hollow primary particle model 14M illustrated in FIG. 12. Thus, the physical quantity of the primary particle model 14M in a solid shape may be set close to that of the primary particle 14 illustrated in FIG. 10, thereby improving the calculation accuracy.

Figure 19:
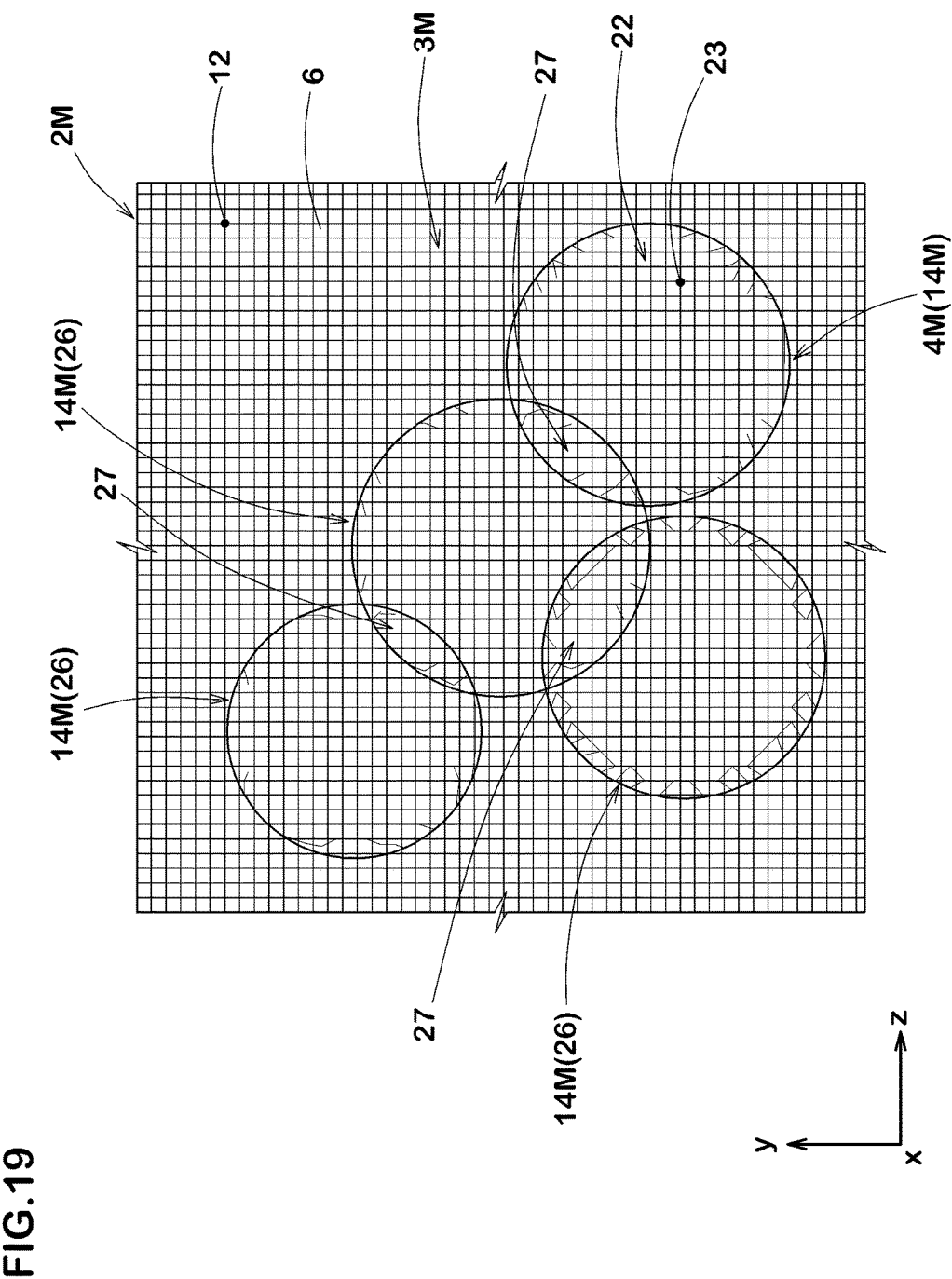
FIG. 19 is a cross-sectional view illustrating a filler compounded rubber models defined using the primary particle model in FIG. 18.

FIG. 19 is a cross-sectional view showing the filler compounded rubber models 2M defined using the primary particle model 14M in FIG. 18. The filler model 4M (the primary particle model 14M), in step S31, is made to arrange in the matrix rubber model 3M without considering sharing of the nodes 12 of the elements 6 of the matrix rubber model 3M and the node 23 of the elements 22 of the primary particle model 14M.

In step S32, a constraint condition between the primary particle models 14M and the matrix rubber model 3M is defined to a first region 26 of the matrix rubber model 3M in which the primary particle model 14M occupies, i.e., the second space T2 in which the filler 4 occupies (shown in FIG. 10B).

The constraint condition in the present embodiment, as with the constraint condition of the previous embodiment illustrated in FIG. 17, a weighting factor of each node 23 is determined based on the geometrical location of each node 23 of the primary particle model 14M with respect to an element 6 of the matrix rubber model 3M, when it has been determined that each node 23 of the primary particle model 14M is present in the element 6 of the matrix rubber model 3M. By using such a weighting factor, the constraint condition between the matrix rubber model 3M and the filler model 4M is defined to create the filler compounded rubber model 2M.

Even such a filler compounded rubber model 2M where the nodes 12 of the matrix rubber model 3M are not shared with the nodes 23 of the primary particle model 14M may offer a transmission of force and displacement through the first region 26 since the constraint condition is set to the first region 26 of the first matrix rubber model 3M in which the primary particle model 14M occupies. Accordingly, the filler compounded rubber model 2M of the present embodiment may maintain the calculation accuracy of the deformation simulation.

Furthermore, in the filler compounded rubber model 2M of the present embodiment, relative movement between the primary particle model 14M and the matrix rubber model 3M is firmly restrained as compared with the filler compounded rubber model which is defined the constraint condition only at the boundary 9 (shown in FIG. 17) according to the prior embodiment, since the constraint condition is define to the first region 26 of the matrix rubber model 3M in which the entire region of each primary particle model occupies. Therefore, the filler compounded rubber model 2M in accordance with the present embodiment can improve the calculation accuracy.

As illustrated in FIG. 19, it is preferable that the weighting factor is calculated for all the nodes 23 of the elements 22 of the primary particle models 14M which include a region 27 where primary particle models 14M are overlapped one another. Thus, the relative movement between each primary particle model 14M and the matrix rubber model 4M can be constrained more strongly, since the constraint condition is set to all of the elements 22 without considering the presence of other primary particle models 14M. Accordingly, it may help to improve the calculation accuracy.

It has been exemplified that the filler compounded rubber model 2M according to the present embodiment is also created as a three-dimensional model, but it may be created as a two-dimensional model. In this case, it is preferable that the matrix rubber model 3M and the primary particle model 14M are created by discretizing using a quadrilateral element or a triangular element (not shown).

Figure 20:
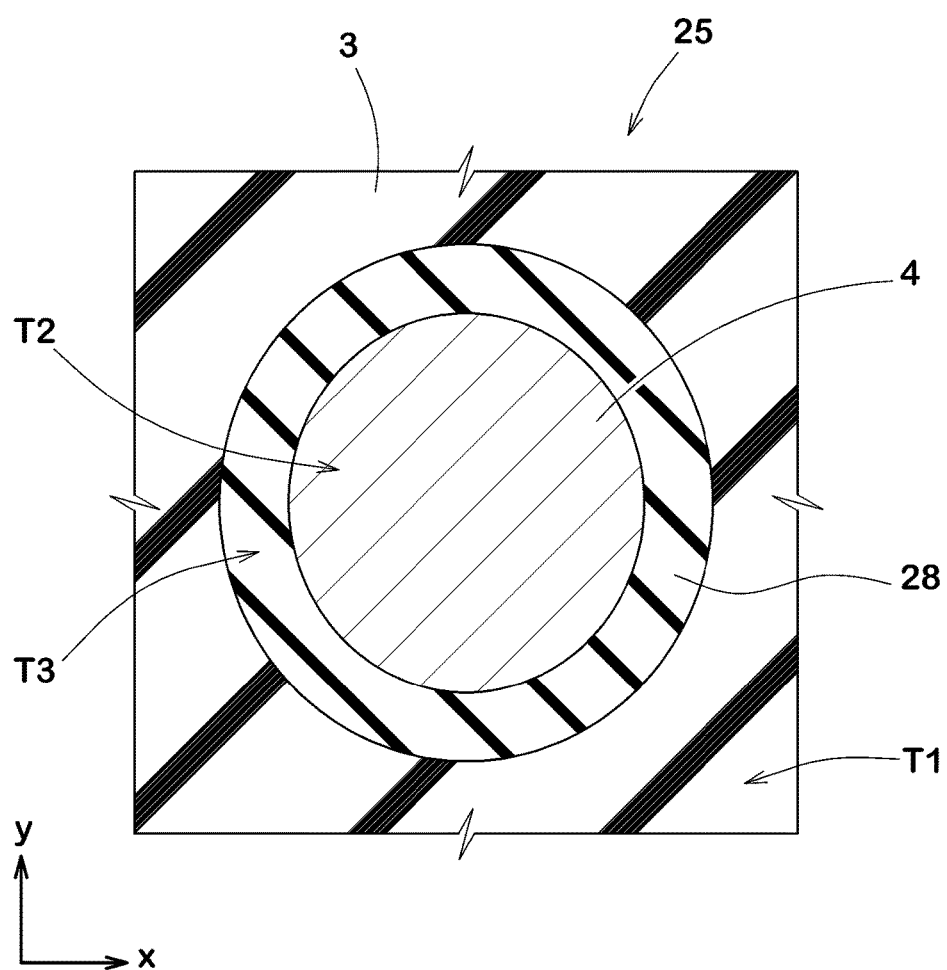
FIG. 20 is a partial enlarged cross-sectional view of the filler compounded rubber in accordance with another embodiment of the present invention.

In the creation method explained through the previous embodiments, it has been explained that the filler compounded rubber model 2M which includes the matrix rubber model 3M and the filler model 4M is set based one the filler compounded rubber 2 (shown in FIG. 2 and FIG. 10) containing a matrix rubber 3 and the filler 4, but it is not limited thereto. FIG. 20 is a partial enlarged cross-sectional view of an example of the filler compounded rubber 25 in accordance with the present embodiment.

The filler compounded rubber 25 in accordance with the present embodiment is expressed in more detailed configuration than the filler compounded rubber 2 illustrated in FIG. 2. The filler compounded rubber 25 is configured to include the matrix rubber 3, the filler 4 and at least one interface layer 28 surrounding the filler 4. In this embodiment, one interfacial layer 28 is exemplified.

Through various experimental results, it has been known that a thin layers exhibiting different mechanical properties from the bulk portion of the matrix rubber 3 is formed around the filler 4. It may also be referred to as the glass layer. The creation method according to the embodiment is suitable to create a finite element model including the interface layer 28 (the filler compounded rubber model).

Figure 21:
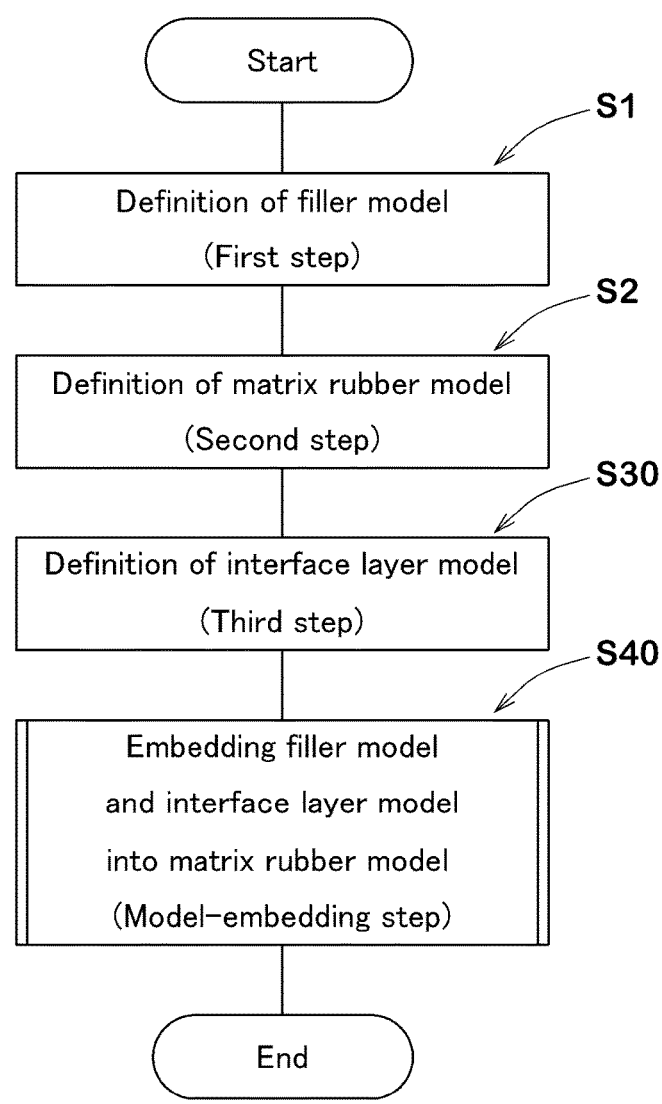
FIG. 21 is a flowchart illustrating a processing procedure of the creation method in accordance with another embodiment of the present invention.

FIG. 21 is a flowchart illustrating a processing procedure of the creation method in accordance with the present embodiment. Through the processing procedure, the computer 1 may create the finite element model (the filler compounded rubber models) of the filler compounded rubber 25 having an interface layer 28 shown in FIG. 20. The filler compounded rubber model of the embodiment is exemplified as a two-dimensional model.

As illustrated in FIG. 21, in the creation method of the embodiment, as with the creation method of the previous embodiments, includes the first step S1 and the second step S2. Thus, the filler model 4M as illustrated in FIG. 4 and the matrix rubber model 3M as illustrated in FIG. 5 are defined. The processing procedure of the steps S1 and S2 are as described in the previous embodiments.

Preferably, in the matrix rubber model 3M according to the present embodiment, as illustrated in FIG. 20, the total space of the first space T1 in which the matrix rubber 3 occupies, the second space T2 in which the filler 4 occupies and a third space T3 in which the interface layer 28 occupies is discretized using elements 6 as illustrated in FIG. 5. That is, in this embodiment, the entire region of the filler compounded rubber 25 to be analyzed is discretized using the elements 6.

Then, the creation method of the present embodiment, the third step S30 is performed. In the third step S30, at least one interface layer 28 surrounding the filler 4 is discretized using a finite number of elements to define an interfacial layer model 28M.

Figure 22:
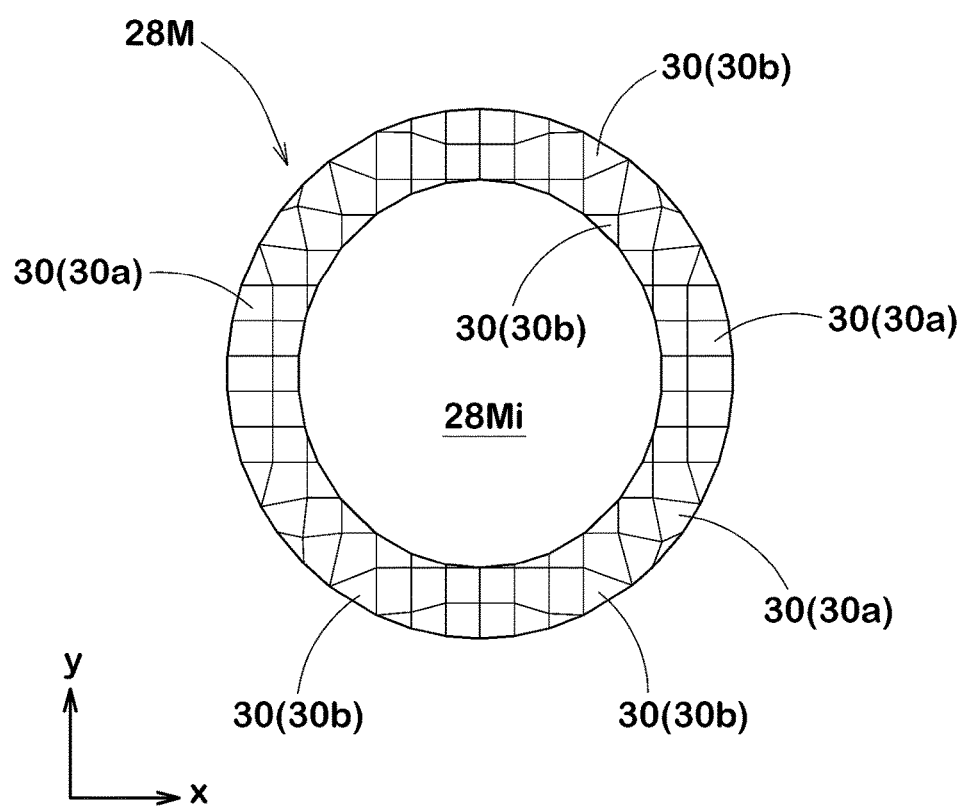
FIG. 22 is a plan view of a visualized interfacial layer model.

FIG. 22 is a plan view of a visualized interfacial layer model. The interfacial layer model 28M is a model obtained by discretizing the space which is approximately equal to a two-dimensional space in which the interface layer 28 occupies in the filler compounded rubber 25, i.e., the third space T3 (FIG. 20) using a plurality of elements 31. Thus, the interface layer model 28M is created in a hollow shape having a void 28Mi therein. The void 28Mi has approximately equal to a volume as the second space T2 in which the filler 4 occupies.

For the elements 30, in case of the two-dimensional model of the present embodiment, for example, a quadrilateral element or a triangular element are suitably used. The interface layer 28 of the present embodiment has an annular circular contour shape. The interface layer model 28M includes a quadrilateral element 30a and a triangular element 30b. It may be possible to define the interface layer model 28M with a smooth circular contour by employing elements 30 having different size and the number of edges thereof.

In the third step S30, the interface layer model 28M is defined independently of the filler model 4M and the matrix rubber model 3M. Here, the expression "be defined independently" in the third step S30 means that the interface layer model 28M is uniquely defined without being associated with the filler model 4M as well as the matrix rubber model 3M. For example, nodes of the interface layer model 28M may be defined at any positions without sharing the nodes of the filler model 4M and the matrix rubber model 3M, thereby improving the degree of freedom of model creation.

Thus, in the creation method of the present embodiment, the filler 4, the matrix rubber 3 and the interfacial layer 28 can be discretized using elements in size or shape appropriate for each. Preferably, the interface layer 28 may be discretized using elements smaller than that of the matrix rubber 3. Thus, the interfacial layer model that reproduces accurately the contour or shape of the interface layer 28 may be defined, and then it would be possible to maintain the calculation accuracy.

The coordinate values of nodes and the element numbers of each element 30 of the interface layer model 28M are stored in the computer 1. In addition, a physical quantity, which may be harder than that of the matrix rubber 3, such as elastic modulus and damping factor based on the physical quantity of the interface layer 28 is inputted in each element 5. The physical quantity is available to calculate deformation of each element 30 (i.e., deformation simulation using the filler compounded rubber model 2M).

In the model-embedded step S40 to be described later, the interface layer model 28M is disposed so as to overlap with the matrix rubber model 3M. The respective values of the physical quantity of the interface layer model 28M correspond to the sum of physical quantity defined in the third step S30 and the physical quantity of the matrix rubber model 3M. Preferably, each value of the physical quantity defined in the interface layer model 28M is set as a value obtained by subtracting each value of the physical quantity of the matrix rubber model 3M from each actual value of the physical quantity of the interfacial layer 28 (shown in FIG. 20). Thus, it may be possible to approach the physical quantity of the interface layer models 28M in the filler compounded rubber model 25M to the actual interfacial layer 28.

Figure 23:
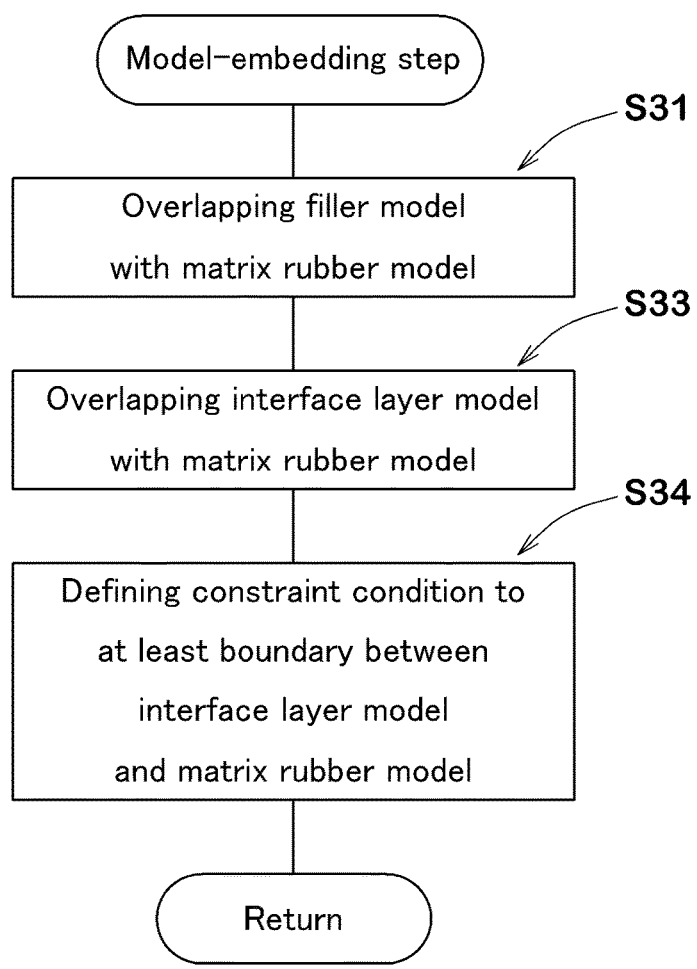
FIG. 23 is a flowchart illustrating an example of a processing procedure of model-embedded step.
Figure 24:
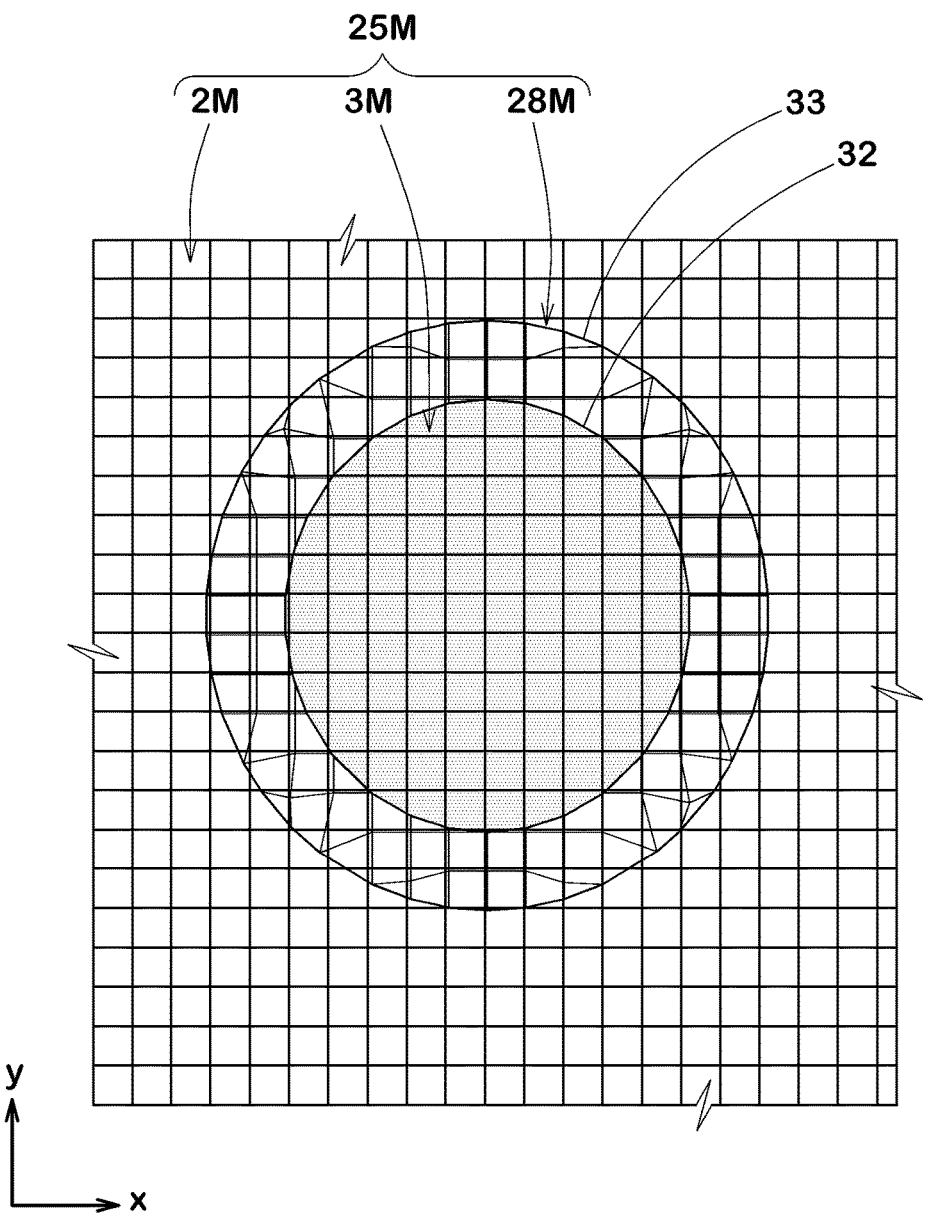
FIG. 24 is a plan view of the filler compounded rubber model.

Then, in the creation method of the present embodiment, as illustrated in FIG. 21, the model-embedded step S40 is performed. In the model-embedded step S40, the filler model 3M and the interface layer model 28M are arranged so as to be embedded into the matrix rubber model 3M. FIG. 23 is a flowchart showing an example of a processing procedure of the model-embedded step S40 of the present embodiment. FIG. 24 is a plan view of the filler compounded rubber model 25M of the present embodiment.

In the model-embedded step S40 in accordance with the present embodiment, as with the previous embodiments, the matrix rubber model 3M and filler models 4M are arranged so as to overlap one another without considering sharing of the respective nodes of the models one another (step S31).

Next, in the model-embedded step S40, the interface layer model 28M is arranged so as to be embedded into the matrix rubber model 3M without considering sharing of the respective nodes of the models one another (step S33). In step S33, the interface layer model 28M is arranged inside the matrix rubber model 3M. The position of the interface layer model 28M to the matrix rubber model 3M is set based on the filler compounded rubber 25 to be analyzed shown in FIG. 20.

Next, in the model-embedded step S40, a constraint condition is given to at least the boundary between the interface layer model 28M and the matrix rubber model 3M (step S34). In step S34 of the present embodiment, the constraint condition is defined to a first boundary 32 between the filler model 4M and the interface layer model 28M as well as a second boundary 33 between the interface layer model 28M and the matrix rubber model 3M. As a result, the filler compounded rubber model 25M is defined.

The method for setting the constraint condition is identical to the embodiment described above.

In the creation method according to the present embodiment, it is possible to save the time and effort for sharing the respective nodes since the matrix rubber model 3M, the filler model 4M and the interfacial layer model 28M are independently defined each other. The creation method of the present embodiment may reproduce accurately the contour or the like of the filler model 4M and the interface layer model 28M while preventing an increase in the number of elements.

Furthermore, the constraint condition is defined to each boundary 32 and 33 of the matrix rubber model 3M, the filler model 4M and the interfacial layer model 28M which are defined independently. In the creation method of the present embodiment, although each node of the matrix rubber model 3M, the filler model 4M and the interface layer model 28M are not shared one another, force and displacement is surely transmitted through each boundary 32 and 33, thereby maintaining the calculation accuracy.

Preferably, the physical quantity defined in the interface layer model 28M are set larger than that of the matrix rubber model 3M and smaller than that of the filler the model 4M. Thus, relative movement of the interface layer model 28M to the matrix rubber model 3M may be allowed partially even when the weighting factor of each node of the element 30 of the interfacial layer model 28M is set same as the weighting factor of the nodes of the elements 5 of the filler model 4M. According to such a filler compounded rubber model 25M, it is possible to effectively reproduce the behavior of the interface layer 28.

Furthermore, the weighting factors of the elements 30 of the interface layer model 28M may be set smaller than that of each node 23 of the element 5 of the filler model 4M. Thus, it is possible to further permit the relative movement of the interface layer model 28M to the matrix rubber model 3M. When the weighting factors of each node of the interface layer model 28M is too small, it may be difficult to constrain sufficiently between the matrix rubber model 3M and the interface layer model 28M. Thus, the overlapping portion between the matrix rubber model 3M and the interface layer model 28M may be forced out from the interface layer model 28M, i.e., the matrix rubber model 3M increases.

It has been exemplified that the filler compounded rubber models 25M of the present embodiment is created as a two-dimensional model, but it may be created as a three-dimensional model. In this case, the matrix rubber model 3M, the fillers model 4M and the interface layer model 28M are preferably created using three-dimensional elements such as a hexahedron element or a tetrahedral element, for example.

Figure 25:
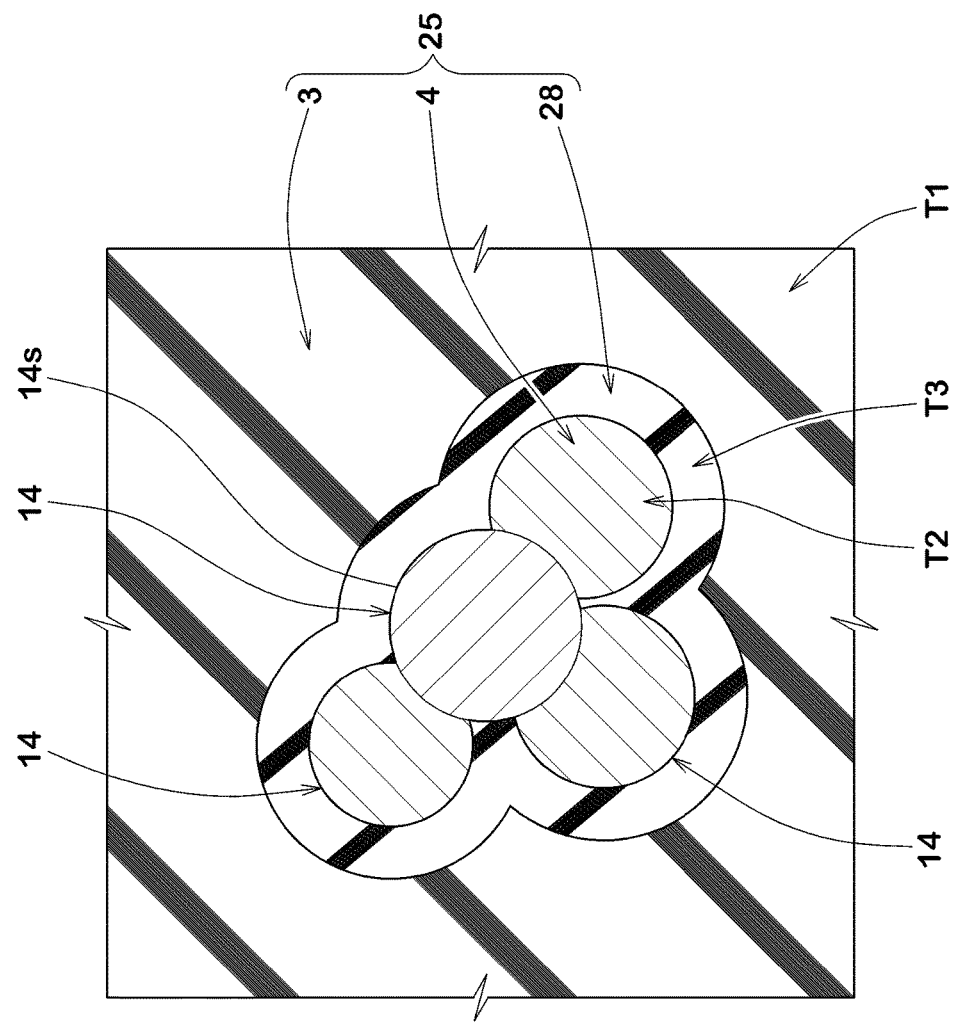
FIG. 25 is a partial enlarged cross-sectional view of the filler compounded rubber in accordance with another embodiment of the present invention.
Figure 26:
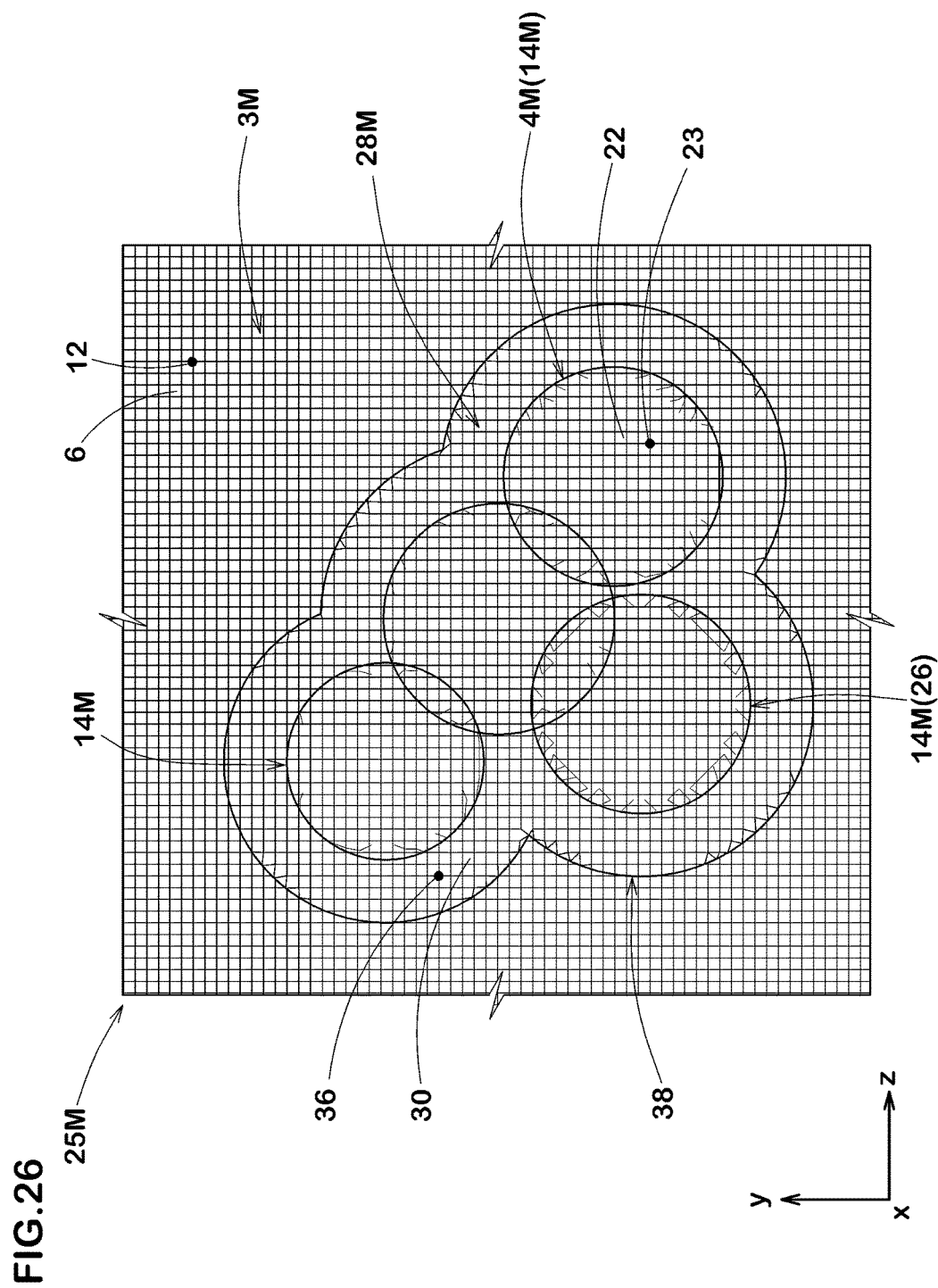
FIG. 26 is a cross-sectional view illustrating the filler compounded rubber model.

FIG. 25 is a partial enlarged cross-sectional view of the filler compounded rubber 25 in accordance with another embodiment of the present invention. FIG. 26 is a cross-sectional view illustrating a filler compounded rubber model in accordance with another embodiment of the present invention.

The filler compounded rubber 25 according to the present embodiment is configured to include the matrix rubber 3, the filler 4 including a plurality of primary particles 14 and a single layer of the interface layer 28 surrounding around the filler 4. In the creation method of the embodiment, the finite element model of the filler compounded rubber 25 as illustrated in FIG. 25 (a filler compounded rubber model) is created. The filler compounded rubber model of the embodiment is created as a three-dimensional model.

In this embodiment, the processing procedure of the creation method is carried out in the same steps of the prior embodiment as illustrated in FIG. 21. In the creation method of the embodiment, the first step S1 is performed. The first step S1 is carried out based on the processing procedure as illustrated in FIG. 11 to create the filler model 4M as illustrated in FIG. 13. In this embodiment, the primary particles 14 are modeled by discretizing using a plurality of three-dimensional elements 22 as illustrated in FIG. 18, but it is not limited thereto. For example, as illustrated in FIG. 12, only the surface 14s of the primary particles 14 may be discretized using a plurality of two-dimensional elements 15.

Furthermore, the creation method of the present embodiment, the second step S2 is performed to create the matrix rubber model 3M as illustrated in FIG. 15. The procedure of the step S2 is the same as described in the previous embodiment. Preferably, the total space of the first space T1 in which the matrix rubber 3 occupies, the second space T2 in which the filler 4 occupies and the third space T3 in which the interface layer 28 occupies is discretized using elements 6 as the matrix rubber model 3M, as illustrated in FIG. 25. That is, according to the present embodiment, the entire region of the inside of the rubber to be analyzed is discretized using the elements 6, as illustrated in FIGS. 15 and 26.

Figure 27:
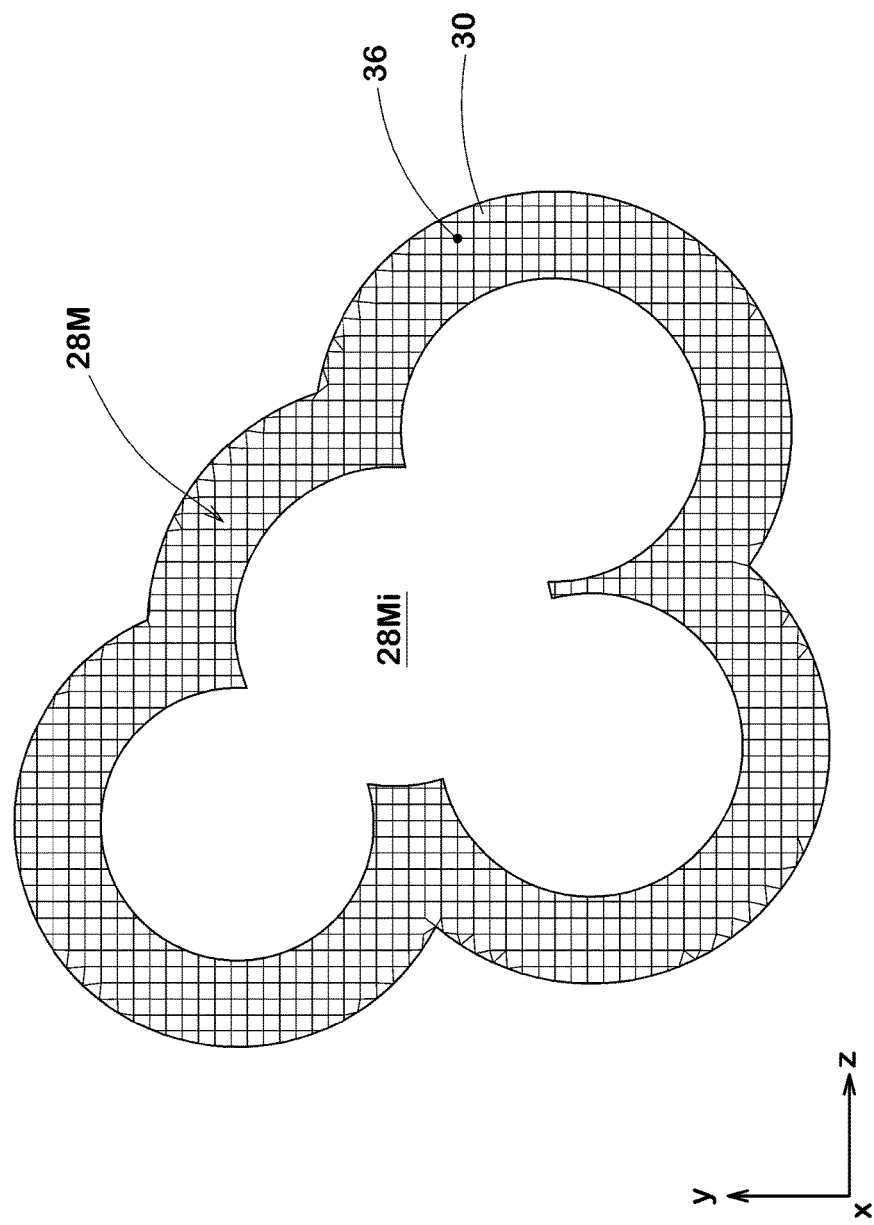
FIG. 27 is a cross-sectional view of the interface layer model.

Then, the creation method of the embodiment, the third step S30 is performed. FIG. 27 is a cross-sectional view of the interface layer model. In the third step S30 of the embodiment, the space which is approximately equal to a three-dimensional space in which the interface layer 28 occupies in the filler compounded rubber 25 (the third space T3 as illustrated in FIG. 20) is discretized using a plurality of elements 30. Thus, a hollow interface layer model 28M having an inner void 28Mi is set. The void 28Mi has a volume almost equal to the second space T2 in which the filler 4 occupies, as shown in FIG. 25.

For the elements 30 of the interface layer model 28M, in case of the three-dimensional model as in the present embodiment, for example, three-dimensional elements are used. For the three-dimensional elements 30, for example, a hexahedron element or a tetrahedral element is preferably used. In this embodiment, both the hexahedral elements and tetrahedral elements are used. For this reason, the interface layer model 28M having a smooth outline can be defined.

The coordinate values of nodes 36 and the element numbers of each element 30 of the interface layer model 28M are stored in the computer 1. Preferably, each value of the physical quantity to be set in the interface layer model 28M, as with the prior embodiments, is defined as a value obtained by subtracting each value of the physical quantity of the matrix rubber model 3M from each actual value of the physical quantity of the interfacial layer 28 (illustrated in FIG. 25).

The interface layer model 28M is created independently of the matrix rubber model 3M and the primary particle model 14M. Thus, each node 36 of the interface layer model 28M may be defined at any arbitrary positions since each node is not necessary to be shared with any nodes 12 of the matrix rubber model 3M as well as nodes 23 of the primary particle model 14M.

Then, in the creation method of the present embodiment, as illustrated in FIG. 21, the model-embedded step S40 is performed. The model-embedded step S40 of the embodiment is performed in the same procedure as the model-embedded step S40 in accordance with the previous embodiment shown in FIG. 23.

In the model-embedded step S40 of the embodiment, as with the previous embodiments, the matrix rubber model 3M and the filler model 4M are placed so as to overlap one another without considering sharing of the respective nodes of the filler model and the matrix rubber model (step S31).

Next, in the model-embedded step S40, the matrix rubber model 3M and the interface layer model 28M are overlapped one another without considering sharing of the respective nodes of the interface layer model and the matrix rubber model (step S33). In step S33, the interface layer model 28M is arranged in the matrix rubber model 3M. The position of the interface layer model 28M to the matrix rubber model 3M is set based on the filler compounded rubber 25 to be analyzed as illustrated in FIG. 25.

Next, in the model-embedded step S40, a constraint condition is given to at least the boundary between the interfacial layer model 28M and the matrix rubber model 3M (step S34). In step S34 of the embodiment, similarly to the prior embodiment illustrated in FIG. 19, the constraint conditions between the matrix rubber model 3M and the primary particle model 14M is defined to the first area 26 of the matrix rubber model 3M in which the primary particle model 14M occupies (i.e., second space T2 in which the filler 4 occupies as shown in FIG. 25). The constraint condition is defined same as described above.

Then, in step S34, the constraint condition between the matrix rubber model 3M and the interface layer model 28M is defined into the second region 38 of the matrix rubber model 3M in which the interface layer model 28M occupies (i.e., the third space T3 in which the interface layer 28 occupies as shown in FIG. 25).

Regarding constraint condition in accordance with the embodiment, as with the constraint condition of the previous embodiments, when the computer 1 is determined that each node 36 of the element 30 of the interface layer model 28M is present in the element 6 of the matrix rubber model 3M, the weighting factor of the concerned node 22 is determined based on the geometry position of the node 36 of the element 30 of the interface layer model 28M to the element 6 of the matrix rubber model 3M. By setting such a weighting factor, the constraint condition between the matrix rubber model 3M and the interface layer model 28M is defined, and then the filler compounded rubber model 25M is created.

Even such a filler compounded rubber model 25M where the nodes 12 of the elements 6 of the matrix rubber model 3M are not shared with the nodes 23 of the primary particle model 14M may offer accuracy a transmission of force and displacement through the first region 26 since the constraint condition is set to the first region 26 of the first matrix rubber model 3M in which the primary particle model 14M occupies. Furthermore, the filler compounded rubber model 25M where the nodes 12 of the elements 6 of the matrix rubber model 3M are not shared with the node 36 of the elements 30 of the interface layer model 28M may offer accuracy a transmission of force and displacement through the second region 38 since the constraint condition is set to the second region 38 of the first matrix rubber model 3M in which the interface layer model 28M occupies. Accordingly, the filler compounded rubber model 25M in accordance with the present embodiment also maintains the calculation accuracy of the deformation simulation.

Furthermore, since the matrix rubber model 3M, the primary particle model 14M and the interfacial layer model 28M are independently defined one another, it can save the time and effort for sharing the respective nodes of models. In the creation method of the embodiment, it is possible to reproduce accurately the surface shape of the primary particle model 14M and the interfacial layer model 28M while preventing an increase in the number of elements.

Preferably, each value of the physical quantity of the interfacial layer model 28M is set larger than that of the matrix rubber model 3M, and is set smaller than that of the primary particle model 14M. Thus, relative movement of the interface layer model 28M to the matrix rubber model 3M may be allowed partially even when the weighting factor of each node 36 of the interface layer model 28M is set same as the weighting factor of the nodes 23 of the primary particle model 14M. According to such a filler compounded rubber model 25M, it is possible to effectively reproduce the behavior of the interface layer 28.

Furthermore, the weighting factor of each node 36 of the interface layer model 28M may be set smaller than that of each node 23 of the primary particle model 14M. Thus, it is possible to further permit the relative movement of the interface layer model 28M to the matrix rubber model 3M. When the weighting factor of each node 36 of the interface layer model 28M is too small, it may be difficult to constrain sufficiently between the matrix rubber model 3M and the interface layer model 28M.

The filler compounded rubber model 25M in accordance with the present embodiment is also exemplified as a three-dimensional structure, but it may be created as a two-dimensional model. In this case, the matrix rubber model 3M, the primary particle model 14M and the interface layer model 28M are preferably discretized using a quadrilateral element or a triangular element (not shown).

While particularly preferred embodiments of the present invention have been described in detail, the present invention is not limited to the embodiments as illustrated, but it may be carried out by modifying to various aspects.

EXAMPLE

Example 1

According to the procedure illustrated in FIG. 3, FIG. 8 and FIG. 11, the filler compounded rubber model as shown in FIG. 16 (Example 1) was defined by modeling the filler compounded rubber as shown in FIG. 10. The primary particle model of Example 1 was obtained by discretizing only the surface of the primary particles of the filler using two-dimensional elements. Then, using the simulation software LS-DYNA, deformation calculation with a 4% elongation in the y-axis direction of the filler compounded rubber model of Example 1 was performed.

Figure 28:
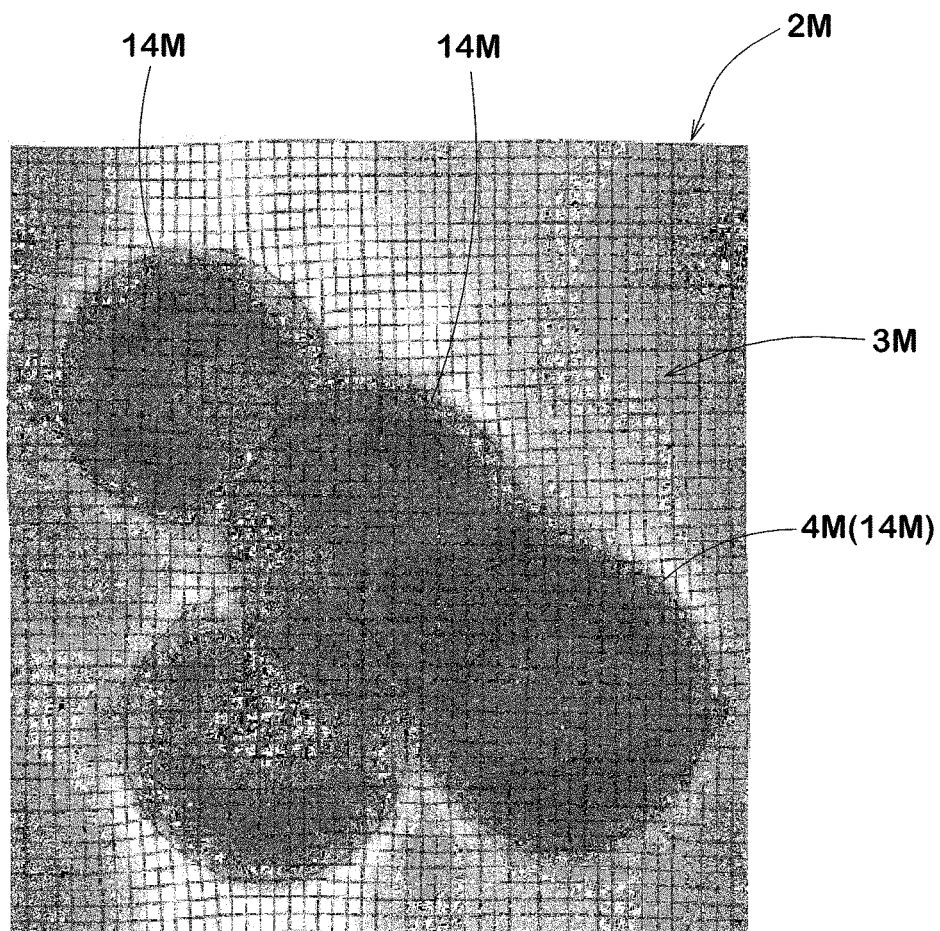
FIG. 28 is a diagram illustrating strain distribution after deformation of the filler compounded rubber model of Example 1.

The result of strain distribution of the filler compounded rubber model of Example 1 is illustrated in FIG. 28.

For comparison, on the basis of the conventional method, a filler model was obtained by discretizing an aggregation of primary particles as shown in FIG. 10 along surface thereof using two-dimensional elements, and then the filler compounded rubber model that contains the filler model was defined (Comparative Example 1). Then, in the same manner as Example 1, the deformation calculation of the filler compounded rubber model of Comparative Example 1 was carried out. The result of strain distribution of the filler compounded rubber model of Comparative Example 1 is illustrated in FIG. 29.

From the test results, it was confirmed that the time required to model the filler compounded rubber model of Example 1 was 83% of the time required to model the filler compounded rubber model of Comparative Example 1. Accordingly, the creation method of Example 1 can create a filler compounded rubber model in a short time as compared with the create method of Comparative Example 1.

Figure 29:
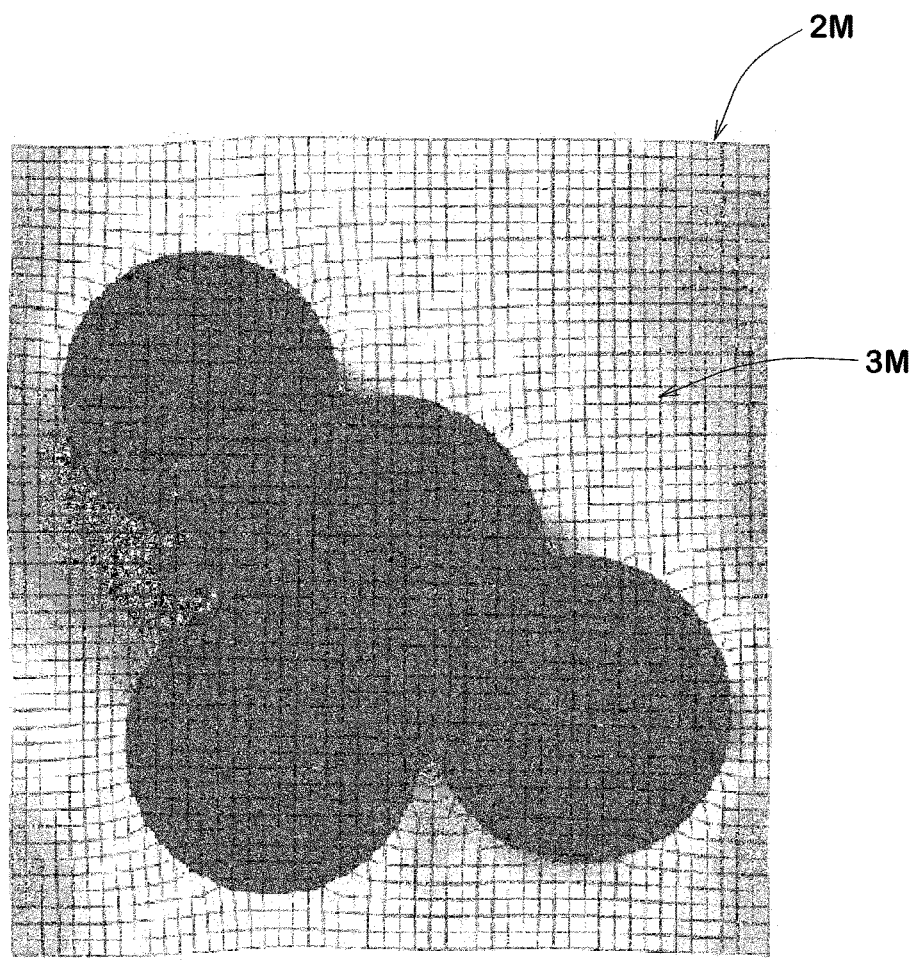
FIG. 29 is a diagram illustrating strain distribution after deformation of the filler compounded rubber model of Comparative Example 1.

Furthermore, as illustrated in FIG. 28 and FIG. 29, it was confirmed that the strain distribution of the filler compounded rubber model of Example 1 was substantially the same as the strain distribution of the filler compounded rubber model of Comparative Example 1. Accordingly, the filler compounded rubber model of Example can maintain the calculation accuracy.

Example 2

According to the procedure illustrated in FIG. 3, FIG. 8 and FIG. 11, the filler compounded rubber model as shown in FIG. 19 (Example 2) was defined by modeling the filler compounded rubber as shown in FIG. 10. The primary particle model of Example 2 was obtained by discretizing using three-dimensional elements. Then, using the simulation software described above, deformation calculation with a 50% elongation in the y-axis direction of the filler compounded rubber model of Example 2 was performed. The result of strain distribution of the filler compounded rubber model of Example 2 is illustrated in FIG. 30.

For comparison, on the basis of the conventional method, a filler model was obtained by discretizing an aggregation of primary particles as shown in FIG. 10 along surface thereof using three-dimensional elements, and then the filler compounded rubber model that contains the filler model was defined (Comparative Example 2). Then, in the same manner as Example 2, the deformation calculation of the filler compounded rubber model of Comparative Example 2 was carried out. The result of strain distribution of the filler compounded rubber model of Comparative Example 2 is illustrated in FIG. 31.

From the test results, it was confirmed that the time required to model the filler compounded rubber model of Example 2 was 55% of the time required to model the filler compounded rubber model of Comparative Example 2. Accordingly, the creation method of Example 2 can create a filler compounded rubber model in a short time as compared with the create method of Comparative Example 2.

Figure 30:
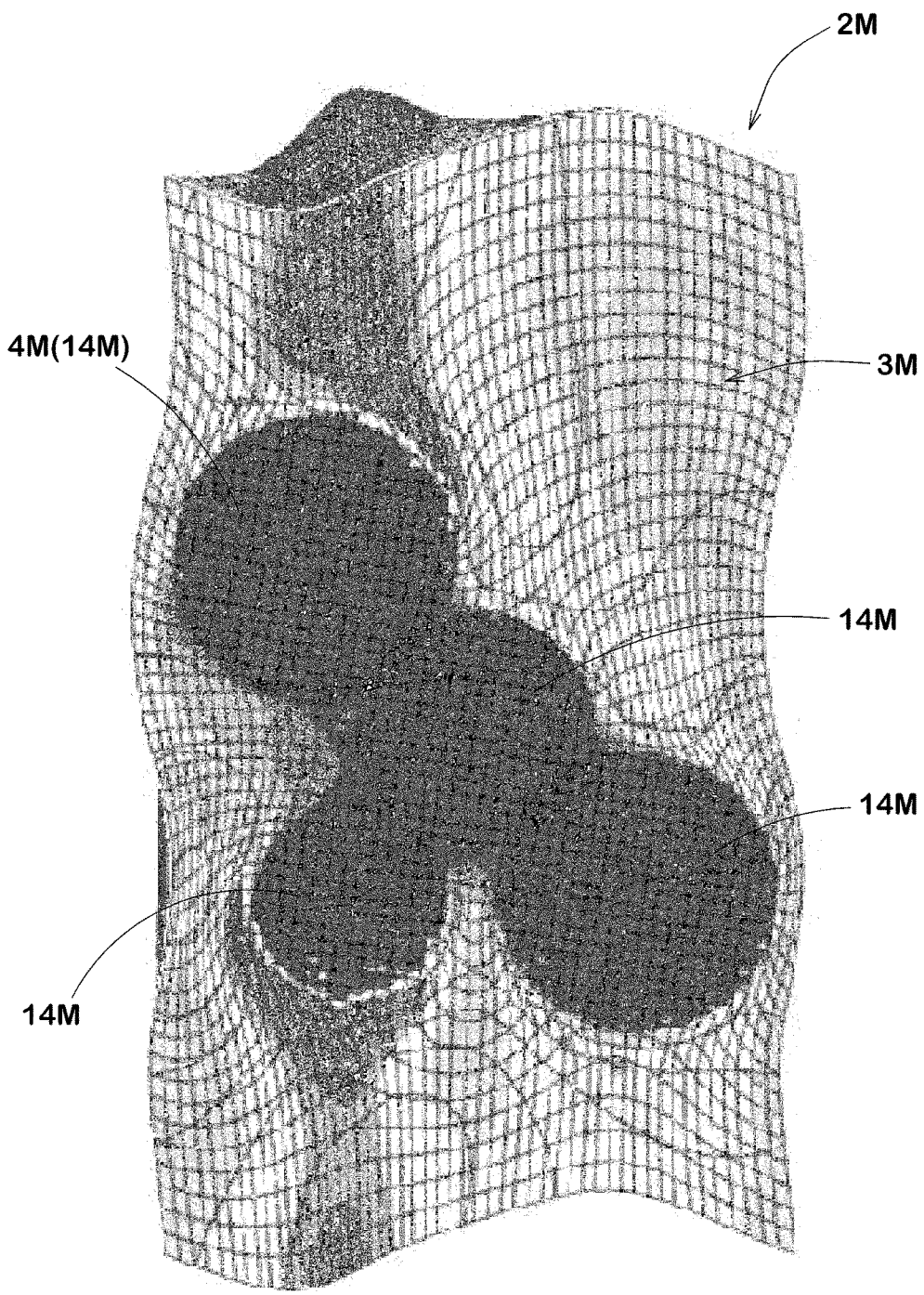
FIG. 30 is a diagram illustrating strain distribution after deformation of the filler compounded rubber model of Example 2.
Figure 31:
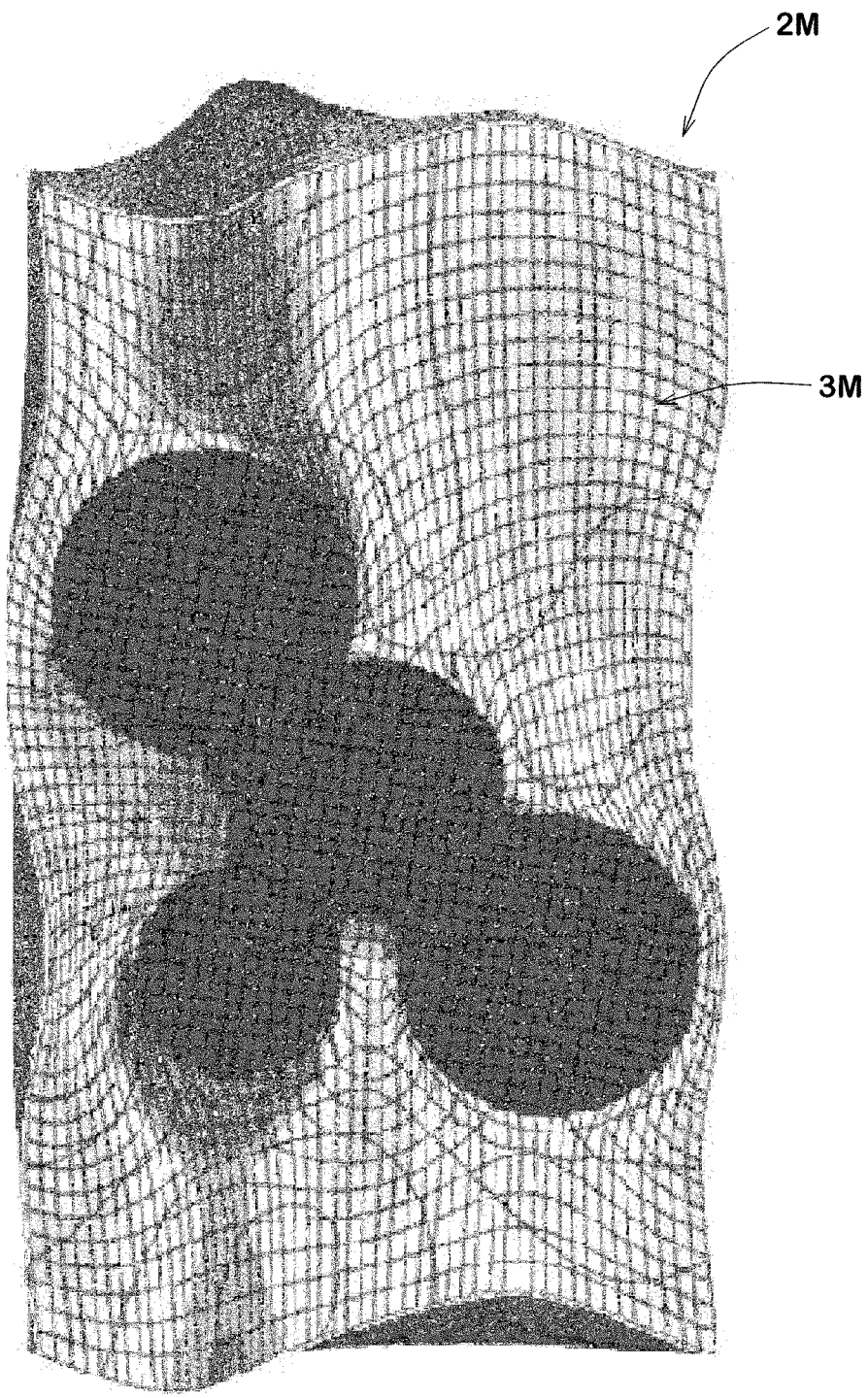
FIG. 31 is a diagram illustrating strain distribution after deformation of the filler compounded rubber model of Comparative Example 2.

Furthermore, as illustrated in FIG. 30 and FIG. 31, it was confirmed that the strain distribution of the filler compounded rubber model of Example 2 was substantially the same as the strain distribution of the filler compounded rubber model of Comparative Example 2. Accordingly, the filler compounded rubber model of Example 2 can maintain the calculation accuracy.

The invention claimed is:

1. A method for creating a finite element model of a filler compounded rubber comprising a filler dispersed in a matrix rubber using a computer, the method comprising:
a first step of defining a filler model in which the filler is discretized using a finite number of elements having nodes;
a second step of defining a matrix rubber model independently of the filler model, the matrix rubber model being created by discretizing a space in which at least the matrix rubber occupies using a finite number of elements having nodes; and
a model-embedded step of embedding the filler-model in the matrix rubber model, wherein the model-embedded step comprises:
a step of overlapping the filler-model with the matrix rubber model without considering sharing of the respective nodes of the filler model and the matrix rubber model so that some nodes of the filler model located on a boundary between the filler model and the matrix rubber model are not shared with the nodes of the matrix model, and
a step of defining a filler compounded rubber model by providing a constraint condition to at least the boundary.

2. The method for creating a finite element model of a filler compounded rubber according to claim 1,
wherein the matrix rubber model is obtained by discretizing a space that comprises a first space in which the matrix rubber occupies and a second space in which the filler occupies, and the model-embedded step comprises the step of defining the constraint condition between the filler model and the matrix rubber model to the second space.

3. The method for creating a finite element model of a filler compounded rubber according to claim 2,
wherein the filler comprises an aggregate of a plurality of primary particles, and the first step comprises a step of defining a plurality of primary particle models each obtained by discretizing each primary particle of the filler using a finite number of elements independently of the matrix rubber model and a step of overlapping the primary particle models one another partially without considering sharing of the respective nodes of the primary particle models.

4. The method for creating a finite element model of a filler compounded rubber according to claim 2,
wherein the method further comprises a third step of defining an interface layer model obtained by modeling at least one interface layer surrounding the filler independently of the filler model and the matrix rubber model,
the third step comprises a step of discretizing the interface layer using a finite number of elements having nodes, and
the model-embedded step comprises the step of overlapping the interface layer model with the matrix rubber model without considering sharing of the respective nodes of the inter face layer model and the matrix rubber model so that some nodes of the interface model located on a boundary between the interface model and the matrix rubber model are not shared with the nodes of the matrix rubber model.

5. The method for creating a finite element model of a filler compounded rubber according to claim 1,
wherein the filler comprises an aggregate of a plurality of primary particles, and the first step comprises a step of defining a plurality of primary particle models each obtained by discretizing each primary particle of the filler using a finite number of elements independently of the matrix rubber model and a step of overlapping the primary particle models one another partially without considering sharing of the respective nodes of the primary particle models.

6. The method for creating a finite element model of a filler compounded rubber according to claim 5,
wherein the method further comprises a third step of defining an interface layer model obtained by modeling at least one interface layer surrounding the filler independently of the filler model and the matrix rubber model,
the third step comprises a step of discretizing the interface layer using a finite number of elements having nodes, and
the model-embedded step comprises the step of overlapping the interface layer model with the matrix rubber model without considering sharing of the respective nodes of the inter face layer model and the matrix rubber model so that some nodes of the interface model located on a boundary between the interface model and the matrix rubber model are not shared with the nodes of the matrix rubber model.

7. The method for creating a finite element model of a filler compounded rubber according to claim 5,
wherein the filler compounded rubber model comprises a three-dimensional model, the matrix rubber model is obtained by discretizing the space using a three-dimensional element, and each primary particle model is obtained by discretizing only an outer surface of each primary particle using a two-dimensional element.

8. The method for creating a finite element model of a filler compounded rubber according to claim 7,
wherein the method further comprises a third step of defining an interface layer model obtained by modeling at least one interface layer surrounding the filler independently of the filler model and the matrix rubber model,
the third step comprises a step of discretizing the interface layer using a finite number of elements having nodes, and
the model-embedded step comprises the step of overlapping the interface layer model with the matrix rubber model without considering sharing of the respective nodes of the inter face layer model and the matrix rubber model so that some nodes of the interface model located on a boundary between the interface model and the matrix rubber model are not shared with the nodes of the matrix rubber model.

9. The method for creating a finite element model of a filler compounded rubber according to claim 5,
wherein the filler compounded rubber model comprises a three-dimensional model, and the matrix rubber model and the primary particle models are obtained by discretizing using the elements of three-dimensional.

10. The method for creating a finite element model of a filler compounded rubber according to claim 9,
wherein the method further comprises a third step of defining an interface layer model obtained by modeling at least one interface layer surrounding the filler independently of the filler model and the matrix rubber model,
the third step comprises a step of discretizing the interface layer using a finite number of elements having nodes, and
the model-embedded step comprises the step of overlapping the interface layer model with the matrix rubber model without considering sharing of the respective nodes of the inter face layer model and the matrix rubber model so that some nodes of the interface model located on a boundary between the interface model and the matrix rubber model are not shared with the nodes of the matrix rubber model.

11. The method for creating a finite element model of a filler compounded rubber according to claim 9,
wherein the elements of the matrix rubber model have different size to the elements of the primary particle models.

12. The method for creating a finite element model of a filler compounded rubber according to claim 11,
wherein the method further comprises a third step of defining an interface layer model obtained by modeling at least one interface layer surrounding the filler independently of the filler model and the matrix rubber model,
the third step comprises a step of discretizing the interface layer using a finite number of elements having nodes, and
the model-embedded step comprises the step of overlapping the interface layer model with the matrix rubber model without considering sharing of the respective nodes of the inter face layer model and the matrix rubber model so that some nodes of the interface model located on a boundary between the interface model and the matrix rubber model are not shared with the nodes of the matrix rubber model.

13. The method for creating a finite element model of a filler compounded rubber according to claim 1,
wherein the method further comprises a third step of defining an interface layer model obtained by modeling at least one interface layer surrounding the filler independently of the filler model and the matrix rubber model,
the third step comprises a step of discretizing the interface layer using a finite number of elements having nodes, and
the model-embedded step comprises the step of overlapping the interface layer model with the matrix rubber model without considering sharing of the respective nodes of the inter face layer model and the matrix rubber model so that some nodes of the interface model located on a boundary between the interface model and the matrix rubber model are not shared with the nodes of the matrix rubber model.

14. The method for creating a finite element model of a filler compounded rubber according to claim 13,
wherein the interface layer model is obtained by discretizing the interface layer using the elements of three-dimensional.

15. The method for creating a finite element model of a filler compounded rubber according to claim 13,
wherein the matrix rubber model is obtained by discretizing a space that comprises a first space in which the matrix rubber occupies, a second space in which the filler occupies and a third space in which the interface layer occupies, and
the model-embedded step comprises the step of defining a constraint condition between the interface layer model and the matrix rubber model to the third space.

16. The method for creating a finite element model of a filler compounded rubber according to claim 13,
wherein the model-embedded step comprises the step of defining a constraint condition to at least a boundary between the interface layer model and the matrix rubber model.

17. The method for creating a finite element model of a filler compounded rubber according to claim 16,
wherein the matrix rubber model is obtained by discretizing a space that comprises a first space in which the matrix rubber occupies, a second space in which the filler occupies and a third space in which the interface layer occupies, and
the model-embedded step comprises the step of defining a constraint condition between the interface layer model and the matrix rubber model to the third space.

18. The method for creating a finite element model of a filler compounded rubber according to claim 16, wherein the interface layer model is obtained by discretizing the interface layer using the elements of three-dimensional.

19. A method for developing a filler compounded rubber, the method comprising:
- a step of creating a filler compounded rubber model according to claim 1;
- a step of performing a deformation calculation of the filler compounded rubber model to obtain stain distribution of the filler compounded rubber model using the computer; and
- a step of outputting a diagram illustrating strain distribution of the filler compounded rubber model after the deformation calculation to evaluate a shape of the filler.

20. A method for creating a finite element model of a filler compounded rubber comprising a filler dispersed in a matrix rubber using a computer, the method comprising:
- a first step of defining a filler model in which the filler is discretized using a finite number of elements having nodes;
- a second step of defining a matrix rubber model independently of the filler model, the matrix rubber model being created by discretizing a space in which at least the matrix rubber occupies using a finite number of elements having nodes; and
- a model-embedded step of embedding the filler-model in the matrix rubber model, wherein the model-embedded step comprises:
  - a step of overlapping the filler-model with the matrix rubber model without considering sharing of the respective nodes of the filler model and the matrix rubber model so that some nodes of the filler model located on a boundary between the filler model and the matrix rubber model are not shared with the nodes of the matrix model, and
  - a step of defining a filler compounded rubber model by providing a constraint condition to at least the boundary; and
- creating an improved finite element model of the filler compounded rubber including the filler model discretized using a smaller element, and the matrix rubber model discretized using a larger and simplified element so as to achieve reduction of calculation cost due to the matrix rubber model while maintaining calculation accuracy due to the filler model having an improved detailed shape.

* * * * *